United States Patent
Isaacs et al.

(10) Patent No.: US 7,335,768 B2
(45) Date of Patent: Feb. 26, 2008

(54) CUCURBIT [N] URIL COMPOUNDS AND ANALOGS, AND METHODS OF MAKING AND USING THE SAME

(75) Inventors: Lyle Isaacs, Bethesda, MD (US); Jason Alan Lagona, Greenbelt, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 10/933,538

(22) Filed: Sep. 3, 2004

(65) Prior Publication Data

US 2005/0080068 A1    Apr. 14, 2005

Related U.S. Application Data

(60) Provisional application No. 60/500,115, filed on Sep. 4, 2003.

(51) Int. Cl.
*C07D 257/10*    (2006.01)

(52) U.S. Cl. .................................................. 540/472

(58) Field of Classification Search ............. 548/303.4; 540/472

See application file for complete search history.

(56) References Cited

OTHER PUBLICATIONS

Day et al. "Controlling Factors in the Synthesis of Cucurbituril and Its Homologues" J. Org. Chem. 2001, 8094-8100.*
Lee et al. "Cucurbituril Homologues and Derivatives: New Opportunities in Supramolecular Chemisty" Acc. Chem. Res. 2003, 621-630.*
PCT/US2006/041116, filed Jul. 24, 2006, Isaacs et al.
PCT/US2006/028841, filed Oct. 20, 2006, Isaacs et al.

* cited by examiner

*Primary Examiner*—Rebecca Anderson
*Assistant Examiner*—Joseph R. Kosack
(74) *Attorney, Agent, or Firm*—William E. Beaumont; Dickinson Wright, PLLC

(57) ABSTRACT

Cucurbit[n]uril compounds each containing phthalhydrazide units in a macrocycle wall thereof, which compound is selected from the group consisting of CB[5], CB[6], CB[7] and CB[8] compounds, the compounds having an internal cavity which may be used to contain a guest compound.

10 Claims, 7 Drawing Sheets

Figure 6. : Conditions: a) DCC, HOBt, b) TFA, CH$_2$Cl$_2$, c) glutaric anhydride, CH$_2$Cl$_2$, Et$_3$N, d) DCC, HOBt, e)TFA, CH$_2$Cl$_2$, f) DCC, HOBt, 54.

CUCURBIT [N] URIL COMPOUNDS AND ANALOGS, AND METHODS OF MAKING AND USING THE SAME

This application claims priority to U.S. Provisional Application No. 60/500,115, filed on Sept. 04, 2003, the complete disclosure of which is herein incorporated by reference.

The work leading up to the present invention was sponsored, at least in part, by National Institutes of Health. As such, the U.S. Government may have certain rights in the invention under 35 USC 203.

BACKGROUND OF THE INVENTION

1. Field of the Invention

The present invention relates to cucurbit [n] uril compounds and methods of making and using the same.

2. Description of the Background

Members of the plant family cucurbitaceae exist in a variety of sizes, shapes and colors. Prime examples include pumpkins, squash, zucchini, cucumbers, cantaloupe, and gourds. The similarity between the molecular shape of the hexameric compound cucurbit [n] uril, i.e. CB[6], and the shape of a pumpkin lead Mock and co-workers to name this compound cucurbituril. In addition to being pumpkin-shaped, the compound CB[6] has two carbonyl-lined portals and a hydrophobic cavity. Through their pioneering work, the groups of Mock and Kim have defined the molecular recognition properties of CB[6] and demonstrated its application in self-assembly studies. Recently, the cucurbituril family gained four new members—CB[5], CB[7], CB[8], and CB[5] @ CB[10] that differ in molecular size from CB[6].

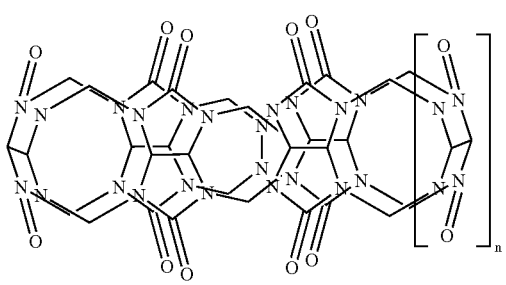

CB[5]   (n = 0)
CB[6]   (n = 1)
CB[7]   (n = 2)
CB[8]   (n = 3)
CB[10]  (n = 5)

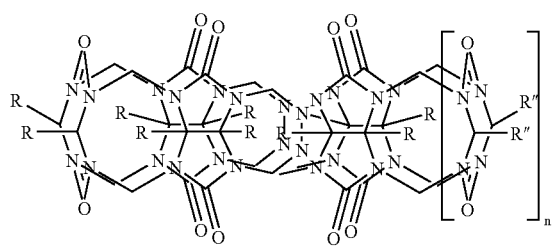

Me$_{10}$CB[5] (R = Me, n = 0)
Cy$_5$CB[5]   (R = R' = R'' = (CH$_2$)$_4$, n = 0)
Cy$_6$CB[6]   (R = R' = R'' = (CH$_2$)$_4$, n = 1)
Ph$_2$CB[1.5] (R = R' = H, R'' = Ph, n = 1)
Me$_6$CB[3.3] (R = H, R' = R'' = Me, n = 1)

CB [5] (diameter: 4.4 Å, volume 82 Å$^3$), CB [6] (diameter: 5.8 Å, volume 164 Å$^3$), CB [7] (diameter: 7.3 Å, volume 279 Å$^3$), and CB [8] (diameter: 8.8 Å, volume 479 Å$^3$) have diameters and cavity volumes that are similar to those of α-, β- and γ-cyclodextrin which suggests their potential broad utility. More over, these compounds have been shown to be amenable to derivatization reactions after formation as recently demonstrated by Kim and co-workers. JACS 2003, 125, 10186-10187.

The preparation of cucurbituril compounds using functionalized glycoluril monomers in CB[n]-forming reactions began shortly after one of Mock's pioneering papers, and resulted in the synthesis of Me$_{10}$ CB[5], Cy$_5$ CB[5], Cy$_6$ CB[6], Ph$_2$ $_{CB}$[1,5], and Me$_6$ $_{CB}$[3,3]. For a review of cucurbit [n] uril homologues and derivatives, see Lee, W. et al. Acc. Chem. Res. 2003, 36, 621-630.

Despite this relative success, no general approach to the synthesis of CB[n] compounds with control over size and functionalization pattern has been reported. Further, currently available CB[n] compounds made by existing synthetic methodologies exhibit poor solubility characteristics and are purified with difficulty. Thus, a need exists for a different approach to the synthesis of CB[n] compounds, which affords control over size and functionalization pattern, as well as improved product solubility and greater ease of purification. Ease of purification is important in as much as current synthetic methodologies for preparing CB[n] compounds are unselective and result in a mixture of CB[n] products requiring separation and purification.

SUMMARY OF THE INVENTION

Accordingly, it is an object of the present invention to provide a method of preparing cucurbit-type compounds using bis (phthalhydrazides) as glycoluril surrogates to control the size, shape and pattern of functional groups in CB[n] forming reactions.

It is also an object of the present invention to provide cucurbit-type compounds containing phthalhydrazide units in a macrocycle wall thereof.

It is a further object of the present invention to provide various methods of using the cucurbit-type compounds of the present invention.

Accordingly, the above objects and others are provided by a cucurbit [n] uril compound having a macrocyclic structure containing phthalhydrazide rings therein, and with chemical functionality on a convex face thereof.

DETAILED DESCRIPTION OF THE PREFERRED EMBODIMENTS

Figure 1:
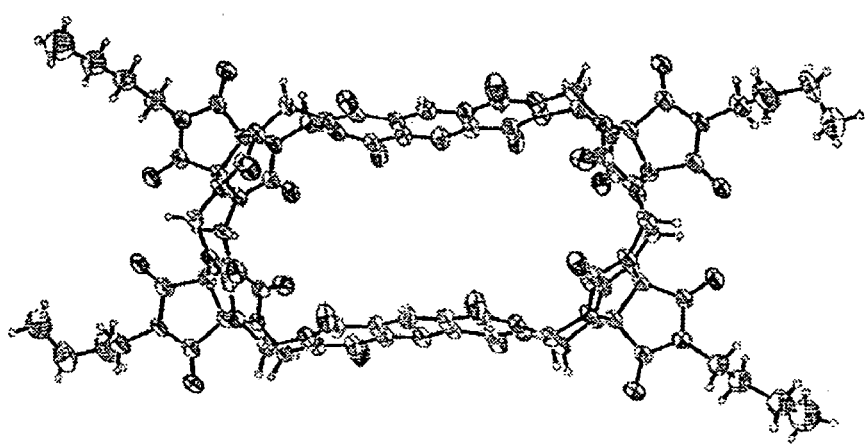
FIG. 1 shows the x-ray crystal structure of the cucurbit [n] uril compound 10 of Scheme 2, wherein R is —$(CO)_2$NBu. Unlike the known pumpkin-shaped CB[n], compound 10 assumes the shape of a cucumber with cavity dimensions of 5.90 Å×11.15 Å×6.92 Å.

The present invention is predicated, in part, upon the discovery that (bis) phthalhydrazides function as well as glycoluril surrogates in the formation of cucurbit [n]uril compounds and related compounds. This approach allows for a tailor-made synthesis of cucurbit[n]uril compounds and related compounds with control over the size, shape, and chemical functionality of the formed cucurbit[n]uril compounds to a level previously not possible.

The present invention provides a building block approach toward various CB[n] compounds, such as CB[5], CB[6] and CB[7] compounds that differ in molecular size, shape, and color from the known CB[n] macrocycles. Specifically, the methods of the present invention afford cucurbit[n]uril, i.e. CB[n], compounds that 1) have good solubility, 2) can be easily tailored for ring size, and shape, and 3) can be provided with specific functionality.

The present invention is based in part on the discovery that phthalhydrazide are potent nucleophiles in condensation reactants with glycoluril cyclic ethers. Thus, we have determined that bis (phthalhydrazide) functions as a surrogate for glycoluril building blocks containing free ureidyl NH groups (e.g. 1 in Scheme 1) in the synthesis of cucurbit [n] uril analogs, and that this approach affords selective heteromeric cyclization reactions that yield control over the pattern of functional groups in CB[n]-forming reactions.

This was demonstrated as depicted on Scheme 1 and Scheme 2 below.

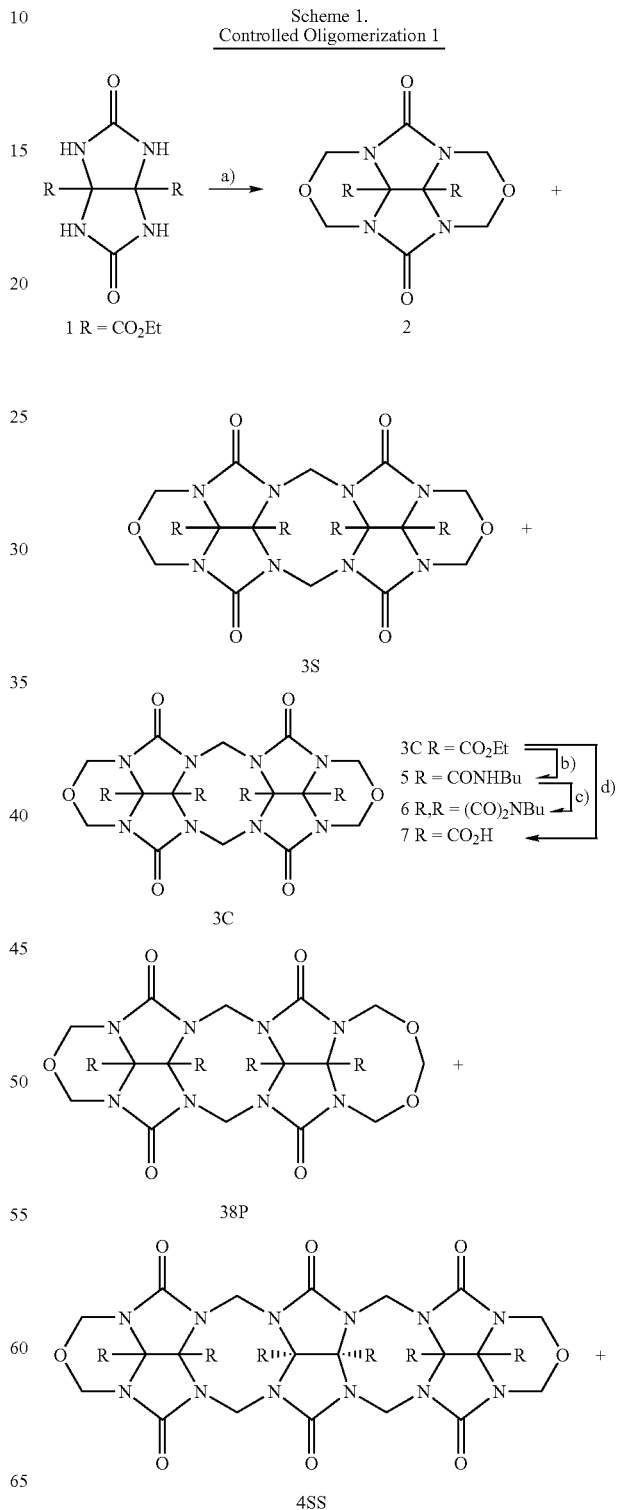

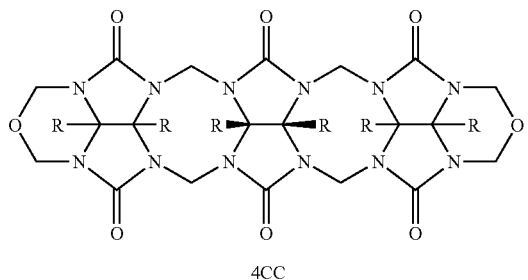

4CC

Scheme 1 depicts the controlled oligomerization of 1 which yielded 2, 3S, 3C, 3BP, 4SS, 4CC and higher oligomers. Through a combination of selective dissolution and chromatographic separations, quantities of 3C, 3S, 4CC and 4SS were obtained. These compounds are distinguishable by spectroscopic means. The transformation of the ethyl ester groups of 3C into amide, imide, and carboxylic acids functional groups (5-7) was effected smoothly by known protocols and procedures.

The reaction conditions for Scheme 1 were as follows: Oligomerization of 1. Conditions: a) ClCH$_2$CH$_2$Cl, PTSA, reflux; b) CH$_3$(CH$_2$)$_3$NH$_2$, 75° C., (68%); c) ClCH$_2$CH$_2$Cl, PTSA reflux (39%); d) LiOH, H$_2$O, CH$_3$OH (89%).

As noted above, from synthetic and mechanistic studies, it was determined that phthalhydrazide 8 (see the below formula) is a potent nucleophile in typical in methylene bridge forming reactions and therefore functions as a surrogate for glycoluril derivatives containing free ureidyl NH groups. To further demonstrate the enhanced nucleophilicity of phthalhydrazides to cucurbit[n]uril analog synthesis, we prepared bis (phthalhydrazide) 8a (see Scheme 2). It was determined that 3C and 8a undergo a smooth reaction in hot anhydrous CH$_3$SO$_3$H yielding CB[6] analog 9 in 78% yield (Scheme 2). Similarly, 6 and 7 bearing imide and carboxylic acid substituents yield 10 and 11 in 70% and 65% yield, respectively. The reaction of 8a with monomeric building block 2 which yields CB [5] analog 12 in 6% yield. Further, the reaction of 8a with methylene bridged glycoluril trimer 4CC was effected to yield CB [7] analog (±)-13 in high yield (67%).

Compound (±)-13 possesses several unusual structural features: 1) it is chiral and racemic due to its C$_2$-symmetry, 2) it contains a single methylene bridge between the two equivalents of 4CC rather than a pair, and 3) this methylene group is directed into the cavity of (±)-13. Compounds 9, 10, 12 and (±)-13 are soluble in polar organic solvents (CHCl$_3$/MeOH, CH$_3$CN, and DMSO) whereas 10 has excellent aqueous solubility. Further, in contrast to all previously reported CB[n] derivatives, compounds 12 and (±)-13 were amenable to purification by simple silica gel column chromatography.

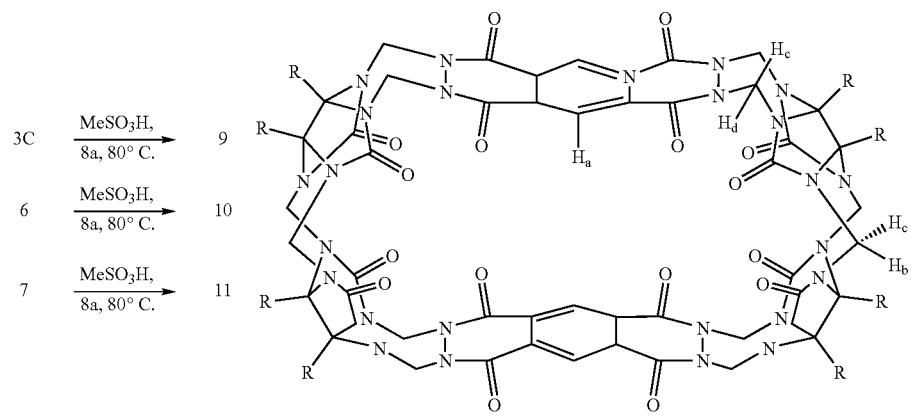

Scheme 2.

9 R = CO$_2$Et; 10 R = (CO)$_2$NBu; 11 R = CO$_2$H

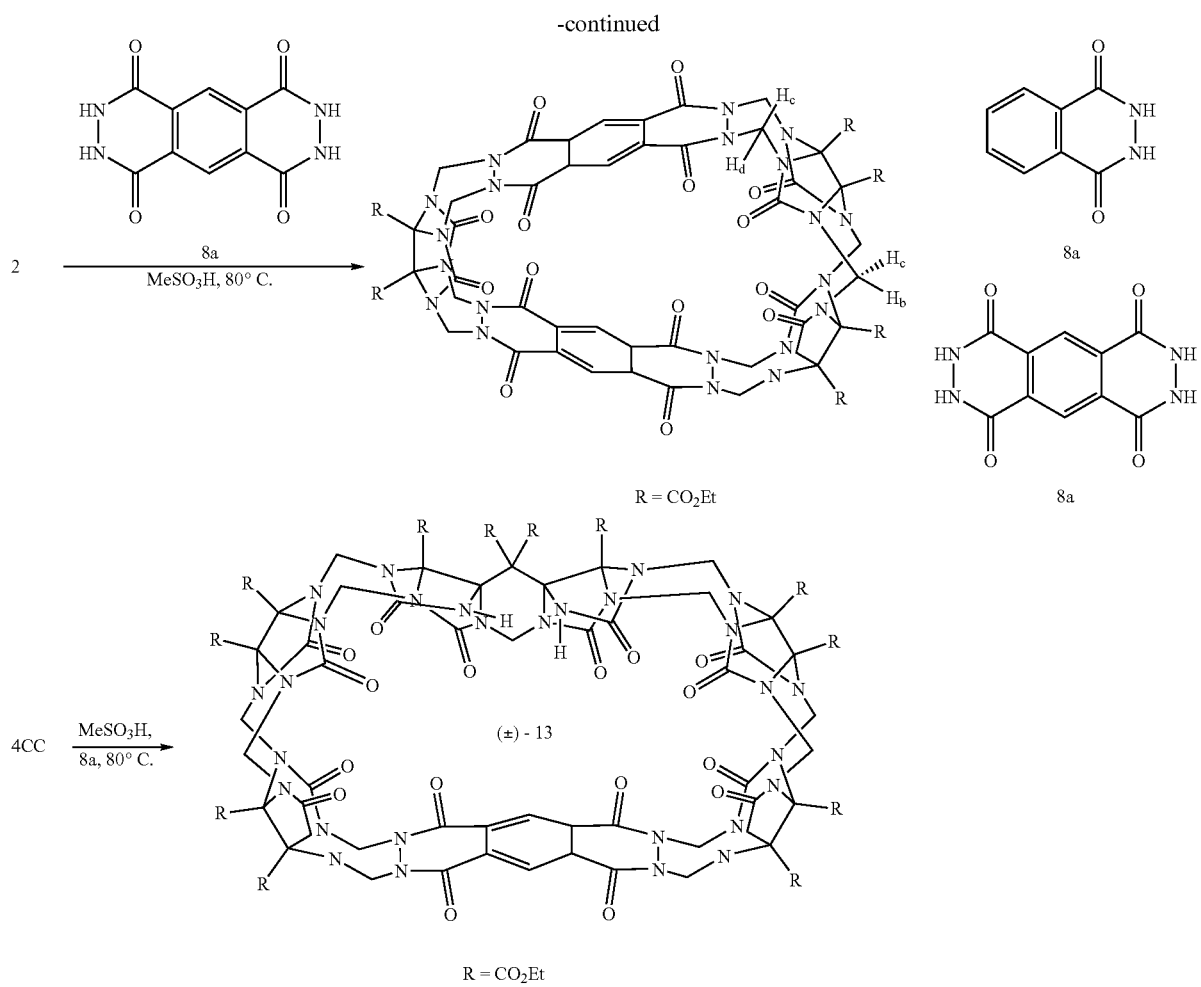

The cucurbit [n] uril or CB[n] compounds of the present invention are well-characterized and readily distinguishable from known CB[n] compounds produced by conventional methodologies, such as those of Mock, Day, and Kim.

Uniformally, the cucurbit [n] uril compound of the present invention incorporate phthalhydrazide rings into their macrocyclic structure which endow these compounds with luminescence and electrochemical activity. Moreover, the present cucurbit [n] uril compounds and analogues incorporate carboxylic acid-based (either acids or esters and/or amides thereof) functionality on their convex face, thereby imparting solubility in polar organic solvents.

Additionally, the present invention affords not only cucurbit[n]uril compounds having phthalhydrazide units in a macrocycle wall thereof, but also such compounds having chirality. Compound (±)-13 is an example of such chiral compounds.

Further, these chiral cucurbit[n]uril compounds may be resolved by conventional chemical resolving system into their respective (+) and (−) enantiomeric components.

FIG. 1 illustrates the x-ray crystal structure of compound 10 of Scheme 2. Unlike known pumpkin-shaped CB[n] made by conventional procedures, compounds 10 of Scheme 2 assumes the shape of a cucumber with cavity diameters of 5.90 Å×11.15 Å×6.92 Å. In the absence of structural information from x-ray diffraction studies, AM1 calculations were performed on compounds 12 and (±)-13 of Scheme 2.

The cavity of compound 12 is shaped like butternut squash with dimension of 5.58 Å×9.75 Å×6.22 Å.

The asymmetric cavity of compound (±)-13 resembles two CB[5] molecules fused together and has dimensions of 5.71 Å×11.34 Å×4.28 Å.

Moreover, as a consequence of having phthalhydrazide units in their macrocyclic walls, all of compounds 9-13 of Scheme 2 differ not only in size and shape, but also in color from known CB[n] compounds prepared by conventional methodologies.

Figure 2:
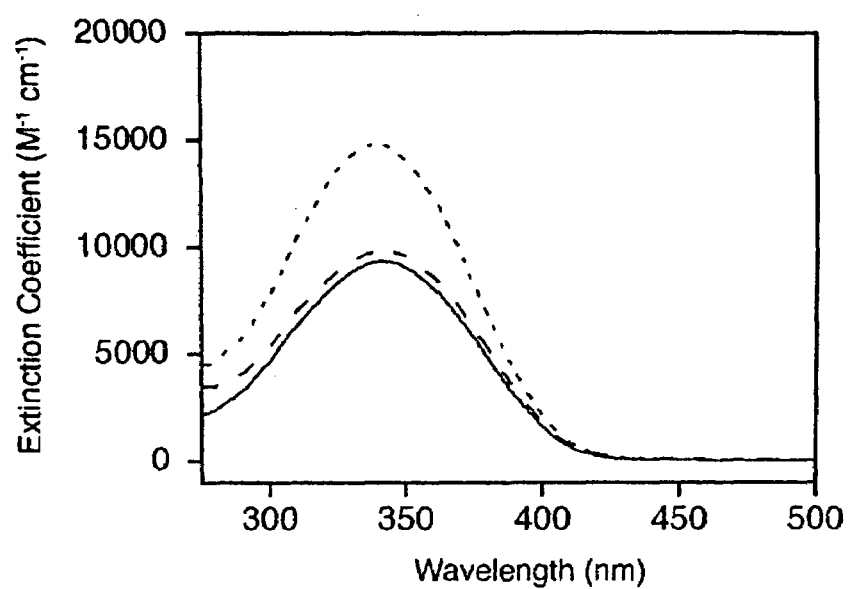
FIG. 2. UV/visible spectra ($CH_3CN$, 298 K) recorded for compounds 9, 12, and (±)-13 of Scheme 2.

Additionally, the cucurbit [n] uril compounds of the present invention are generally characterized by showing a broad (a half peak width of at least 50-75 nm) UV/visible absorption in $CH_3CN$ with $\lambda_{max}$ at 342 nm. For example, see FIG. 2 for compounds 9, 12 and (±)-13.

Figure 3:
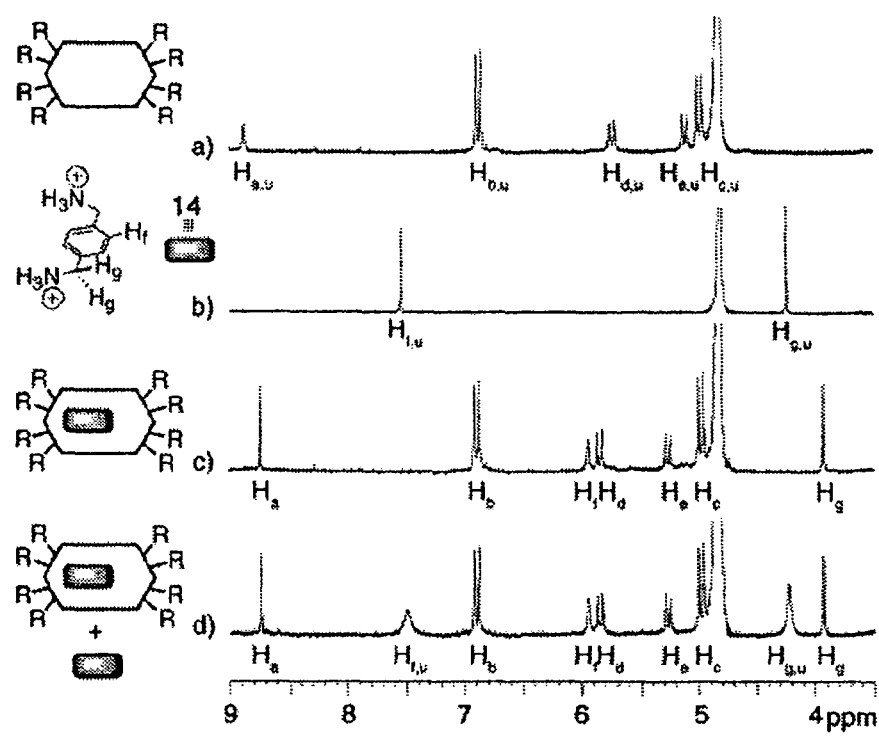
FIG. 3. $^1H$ NMR spectra recorded (50 mM acetate buffered $D_2O$, pD 4.9, 298 K, 400 MHz) for: a) 12 1.2 mM), b) 15 (1.2 mM), c) a mixture of 12 (1.2 mM) and 15 (1.2 mM), and (d) a mixture of 12 (1.2 mM) and 15 (4.8 mM). Protons attached to uncomplexed host and guest are indicated with a subscript (u).

The structural relationship between CB[n] and 9-13 suggests that the CB[n] analogs possess similar recognition properties. Similar to CB[8], the cavities of 9-13 are spacious and possess two binding sites which allows for termolecular complex formation. FIGS. 3a and 3b show the $^1H$ NMR spectra of 11 and p-xylylene diamine (14) recorded separately. The $^1H$ NMR spectrum of a 1:1 mixture of 11 and 14 (FIG. 3c) shows significant upfield shifts for the aromatic ($H_f$) and methylene ($H_g$) protons of 14 in accord with their proximity to the shielding region defined by the bis(phthalhydrazide) walls of 11. FIG. 3d shows the $^1$H NMR spectrum recorded for a 1:4 mixture of 11 and 14 which demonstrates that chemical exchange between free and bound guest is slow on the chemical shift time scale. Integration of the resonances for host versus bound guest allows us to establish the 1:1 stoichiometry of the 11•14 complex. Despite the fact that the cavity of 12 is too small to accommodate two equivalents of 14, examination of CPK models suggested that it is spacious enough to accommodate two equivalents of hexanediamine (16). $^1$H NMR experiments indicate that while 16 does bind within 12, it also does so with a 1:1 stoichiometry.

Thus, the present invention provides a facile synthesis of CB[n] compounds, such as CB[5], CB[6] and CB[7] analogs based on the condensation of nucleophilic glycoluril surrogate 8a with glycoluril bis (cyclic ethers) bearing ester, imide, and carboxylic acid functional groups. Although we have used bis(phthalhydrazide) 8a was described above, the use of longer, non-planar and functionalized bis(phthalhydrazides) in CB[n] analog forming reactions is also specifically contemplated to deliver further control over the size, shape and recognition properties of CB[n] analogs.

For example, bis (phthalhydrazides) of the general formulae:

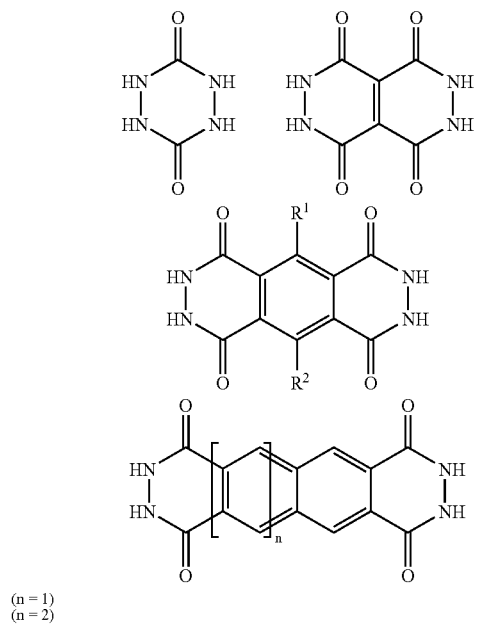

(n = 1)
(n = 2)

may be used, wherein R is H, Br, NH$_2$, or —OR, or —CO$_2$R, where R is lower alkyl for example. However, any bis- or multi (phthalhydrazide) compounds may be used in order to incorporate phthalhydrazide units in the macrocycle wall of the cucurbit [n] uril compound formed.

For example, the lower alkyl ester or lower alkyl amide group may be substituted by one or more hydroxyl, halo, nitro, lower alkyl or lower alkyl ether groups. As used herein and throughout this disclosure, the term "lower" means from 1 to 20 carbon atoms, preferably from 1 to 10 carbon atoms, and most preferable from 1 to 6 carbon atoms.

Alternately, compounds of the general formulae:

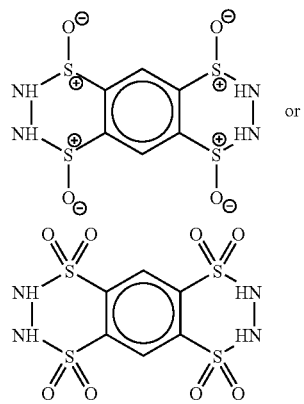

may also be used in the formation of cucurbit [n] uril compounds inasmuch as they function similarly to bis (phthalhydrazides).

In using bis (phthalhydrazides) to prepare cucurbit [n] uril compounds, a "building block approach" is used to form single cucurbit [n] uril compounds (analogs) in high yield.

Experimental Procedures:

General. Starting materials were purchased from Alfa-Aesar, Acros, and Aldrich and were used without further purification. Compounds 1 and 8 were prepared by literature procedures. TLC analysis was performed using pre-coated glass plates from E. Merck. Column chromatography was performed using silica gel (230-400 mesh, 0.040-0.063 μm) from E. Merck using eluents in the indicated v:v ratio. Melting points were measured on a Meltemp apparatus in open capillary tubes are uncorrected. IR spectra were recorded on a Nicolet Magna spectrophotometer as KBr pellets or thin films on NaCl plates and are reported in cm$^{-1}$. UV/Vis spectra were recorded on an Agilent 8453 diode array spectrophotometer. NMR spectra were measured on Bruker AM-400 and DRX-400 instruments operating at 400 MHz for $^1$H and 100 MHz for $^{13}$C. Mass spectrometry was performed using a VG 7070E magnetic sector instrument by fast atom bombardment (FAB) using the indicated matrix. The matrix "magic bullet" is a 5:1 (w:w) mixture of dithiothreitol:dithioerythritol. Elemental analyses were performed by Midwest MicroLab (Indianapolis, Ind.).

Synthetic Procedures and Characterization.

Oligomerization of 1: A mixture of PTSA (33.23 g, 174-7 mmol) and ClCH$_2$CH$_2$Cl (500 mL) was heated at reflux for 30 min. under an addition funnel filled with molecular sieves (4 Å). Compound 1$^1$ (10.00 g, 34.95 mmol) was added and allowed to dissolve completely. Then, paraformaldehyde (5.25 g, 174.7 mmol) was added and reflux was continued for 2 h. The reaction mixture was diluted with EtOAc (800 mL), washed with sat. Na$_2$CO$_3$, derived over anh. MgSO$_4$ concentrated, and the residue was dried under high vacuum. Flash chromatography (SiO$_2$, 10:1 CHCl$_3$/CH$_3$CN) gave 2 (3.58 g, 9.78 mmol, 28%), 3S (0.394 g, 0.579 mmol, 3.3%, 3C (9.579 g, 0.851 mmol, 5.0%), and 4SS (0.164 g, 0.165 mmol, 1.4%) all as white solids. The mobile phase was changed to 5:1 CHCl$_3$/CH$_3$CN to give the impure 3BP as a white solid that was recrystallized from MeOH to yield 3BP (0.026 g, 0.037 mmol, 0.21%). Impure 4CC was isolated as an off-white solid. The solid was washed with a small amount of EtOAc, centrifuged, and dried to give 4CC as a white powder (0.120 g, 0.121 mmol, 1.0%).

Compound 2. Spectroscopic data matched the literature values. See Isaacs, L; Witt, O.; and Fettinger, J. C., Chem. Commun. 1999, 2549-2550.

Compound 3S: M.p. 235° C. TLC (CH$_2$Cl$_2$/CH$_3$CN, 10:1) R$_f$ 0.33. IR (KBr, cm$^{-1}$): 3002w, 2983w, 2959w, 2897w, 1751s, 1728s, 1476m, 1425m, 1410s, 1383m, 1278s, 1239m, 1169m, 1084m, 1033m, 1010s. $^1$H NMR (400 MHz, CDCl$_3$): 5.49 (d, J=11.2, 4H), 5.24 (s, 4H), 4.68 (d, J=11.2, 4H), 4.30-4.20 (m, 8H), 1.28 (t, J=7.2, 12 H). $^{13}$C NMR (100 MHz, CDCl$_3$): 164.7, 163.7, 155.6, 79.2, 75.4, 72.6, 64.6, 63.9, 52.4, 13.9, 13.6. MS (FAB, Magic Bullet): m/z 681 (20, [M+H]$^+$), 45 (100, C$_2$H$_5$O$^+$). HR-MS (FAB, Magic Bullet): m/z 681.2125 ([M+H]$^+$, C$_{26}$H$_{33}$N$_8$O$_{14}$, calcd 681.2116). X-ray crystal structure. Crystals obtained from EtOH.

Compound 3C: M.p. 247-249° C. TLC (CHCl$_3$/CH$_3$CN, 4:1) R$_f$ 0.35. IR (KBr, cm$^{-1}$); 2983w, 2967w, 1759s, 1643w, 1472m, 1427m, 1367w, 1301m, 1243s. $^1$H NMR (400 MHz, CDCl$_3$): 6.01(d, J=16.0, 2H), 5.53 (d, J=11.0, 4H), 4.87 (d, J=16.0, 2H), 4.73 (d, J=11.0, 4H), 4.30-4.20 (m, 8H), 1.35-1.25 (m, 12H). 13C NMR (100 MHz, CDCl3): 164.8, 164.4, 155.1, 78.9, 73.7, 72.7, 64.0, 63.7, 48.2, 13.9 (only 10 of the 11 expected resonances were observed). MS (FAB, Magic Bullet): m/z 681 (100, [M+H]$^+$). HR-MS (FAB, Magic Bullet): m/z 681.2127 ([M+H]$^+$, C$_{26}$H$_{33}$N$_8$O$_{14}$, calcd 681.2116). Anal. Calcd for C$_{26}$H$_{32}$N$_8$O$_{14}$ (680.58): C 58.88, H4.74. Found: C 45.48, H 4.62. X-ray crystal structure. Crystals obtained from a mixture of CHCl$_3$/CH$_3$CN (1:1).

Compound 3BP: M.p. 287-288° C. TLC (CHCl$_3$/CH$_3$CN, 3:1) R$_f$ 0.26. IR (KBr, cm$^{-1}$): 2986w, 2967w, 1751s, 1631w, 1456m, 1433m, 1293m, 1258m, 1169w, 1107m, 1087m, 1021m, $^1$H NMR (400 MHz, CDCl$_3$): 6.07 (d, J=16.0, 2H), 5.51 (d, J=10.8, 2H), 5.42 (br. s, 2H), 4.85 (br. s, 4H), 4.73 (d, J=10.8, 2H), 4.61 (d, J=16.0, 2H), 4.30-4.15 (m, 8H), 1.35-1.25 (m, 12H). 13C NMR (100 MHz, CDCl$_3$): 164.9, 164.7, 164.6, 164.4, 155.0, 154.5, 80.0, 78.9, 78.9, 78.4, 74.1, 74.0, 72.7, 64.2, 63.8, 63.6, 63.5, 48.0, 13.9, 13.8 (only 19 of the 22 expected resonances were observed). MS (FAB, Magic Bullet): m/z 711 (70, [M+H]$^+$), 681 (100, [M—CH$_2$CH$_3$]+). HR-MS (FAB, Magic Bullet): m/z 711.2240 ([M+H]$^+$, C$_{27}$H$_{35}$N$_8$O$_{15}$, calcd 711.2222).

Compound 4SS: M.p. 232-233° C. TLC (CHCl$_3$/CH$_3$CN, 3:1) R$_f$ 0.22. IR (KBr, cm$^{-1}$): 2986w, 2936w, 1755s, 1744s, 1631w, 1472m, 1456m, 1421m, 1382m, 1293m, 1250m, 1084m, 1014m, $^1$H NMR (400 MHz, CDCl$_3$): 5.48 (d, J=11.0, 4H), 5.38 (d, J=13.8, 4H), 4.98 (d, J=13.8, 4H), 4.72 (d, J=11.0, 4H), 4.30-4.20 (m, 8H), 4.14 (q, J=7.2, 4H), 1.35-1.25 (m, 18H). $^{13}$C NMR (100 MHz, CDCl$_3$): 164.5, 164.0, 163.5, 155.2, 154.9, 79.7, 79.5, 74.1, 72.7, 65.0, 64.4, 63.8, 51.5, 13.9, 13.8, 13.5. MS (FAB, Magic Bullet): m/z 991(100, [M+H]$^+$). HR-MS (FAB, Magic Bullet): m/z 1123.2004 ([M+Cs]$^+$, C$_{38}$H$_{46}$N$_{12}$O$_{20}$Cs, calcd 1123.2006).

Compound 4CC: M.p. 290-293° C. TLC (CHCl$_3$/MeOH, 5:1) R$_f$ 0.35. IR (KBr, cm$^{-1}$): 2963s, 2901w, 1755m, 1634w, 1437w, 1293w, 1258s, 1091s, 1021s. $^1$H NMR (400 MHz, CDCl$_3$): 6.15 (d, J=16.0, 4H), 5.53 (d, J=10.8, 4H), 4.73 (d, J=10.8, 4H), 4.72 (d, J=16.0, 4H), 4.25-4.15(m, 12H), 1.35-1.25 (m, 18H). $^{13}$C NMR (100 MHz, CDCl$_3$): 164.9, 164.6, 154.8, 154.8, 154.3, 79.6, 78.9, 73.9, 72.6, 64.2, 63.5, 48.5, 13.9, 13.8 (only 14 of the 16 expected resonances were observed). MS (FAB, Magic Bullet): m/z 991 (100, [M+H]$^+$). HR-MS (FAB, Magic Bullet): m/z 1123.1971 ([M=Cs]$^+$, C$_{38}$H$_{46}$N$_{12}$O$_{20}$Cs, calcd 1123.2006).

Compound 5: A flask containing compound 3C (0.134 g, 0.197 mmol) was flushed with N$_2$ and then n-butylamine (26 mL) was added. The reaction mixture was sonicated and then heated at 75° C. for 24 h. The reaction mixture was concentrated and dried under high vacuum. The resulting residue was washed with Et$_2$O and dried. The less polar impurity was removed using a fritted filter funnel filled with SiO$_2$ (CHCl3/CH$_3$CN 10:1). The SiO$_2$ containing the desired product was stirred in a mixture of CHCl$_3$/MeOH (5:1, 100 mL) for 24 h. The mixture was filtered and the filtrate was concentrated to give 5 as a white solid (0.105 g, 0.133 mmol, 68%). M.p. >350° C. (dec). TLC (CHCl$_3$/MeOH, 10:1) R$_f$ 0.11. IR (KBr, cm$^{-1}$): 3445s, 3045w, 2963m, 2932m, 2874w, 1751s, 1697s, 1538m, 1472m, 1433s, 1375m, 1301m, 1255m, 1189w, 1118m, 1096m, 1017m, 1009m. $^1$H NMR (400 MHz, DMSO-d$_6$): 8.59 (t, J=5.4, 2H), 8.29 (t, J=5.4, 2H), 5.61 (d, J=16.0, 2H), 5.25 (d, J=11.2, 2H), 4.55 (d, J=16.0, 2H), 4.51 (d, J=11.2, 2h), 3.05-3.00 (m, 4H), 2.95-2.90 (m, 4H), 1.40-1.30 (m. 8H), 1.25-1.15 (m, 8H), 0.86(t, J=7.2, 6H), 0.85(t, J=7.2, 6H). $^{13}$C NMR (100 MHz, CDCl$_3$/MeOH (20:1)): 163.7, 161.6, 155.7, 80.6, 74.9, 48.4, 40.7, 40.5, 31.0, 30.8, 20.2, 20.0, 13.6 (only 14 of the 15 expected resonances were observed). MS (FAB, MNBA): m/z 811 (100, [M+Na]$^+$), 789 (30, ([M+H]$^+$). HR-MS (FAB, MNBA/PEG): m/z 789.3989 ([M+H]$^+$, C$_{34}$H$_{53}$N$_{12}$O$_{10}$, calcd 789.4008).

Compound 6: To a mixture of 5 (0.140 g, 0.178 mmol) and PTSA (0.170 g, 0.888 mmol) was added ClCH$_2$CH$_2$Cl (30 mL). The reaction mixture was heated at reflux for 48 h, cooled, concentrated, and dried under high vacuum. The resulting residue was washed with water and dried under high vacuum. Flash chromatography (10:1 CHCl$_3$/CH$_3$CN) gave 6 as a white solid (0.044 g, 0.069 mmol, 39%). M.p. >350° C. (dec). TLC (CHCl$_3$/CH$_3$CN, 10:1) R$_f$ 0.32. IR (KBr, cm$^{-1}$): 2960w, 2935w, 1924w, 2874w, 1781s, 1759m, 1720s, 1472m, 1422s, 1372s, 1302s, 1263m, 1016m. $^1$H NMR (400 MHz, CDCl$_3$): 5.73 (d, J=15.5, 2H), 5.52(d, J=11.0, 4H), 5.30(d, J=15.5, 2H), 5.03 (d, J=11.0, 4H), 3.59 (t, J=7.4, 4H), 1.65-1.50 (m, 4H), 1.35-1.25(m, 4H), 0.93 (t, J=7.6, 6H). $^{13}$C NMR (100 MHz, CDCl$_3$): 167.5, 166.4. 154.5, 72.7, 71.9, 70.1, 46.5, 39.5, 29.2, 20.0, 13.5. MS (FAB, Magic Bullet/PEG): m/z 643 (100, [M+H]$^+$). HR-MS (FAB, Magic Bullet/PEG): m/z 643.2229 ([M+H]$^+$, C$_{26}$H$_{31}$N$_{10}$O$_{10}$, calcd 643.2225). X-ray crystal structure. Crystals obtained from a mixture of CH$_3$CN/MeOH (5:1).

Compound 7: To a flask containing 3C (0.200 g, 0.294 mmol) and LiOH (0.0707 g, 2.94 mmol) was added distilled water (50 mL) and MeOH (50 mL). The flask was sealed and the reaction mixture was heated at 70° C. for 24 h. The reaction mixture was cooled to RT, concentrated, and dried under high vacuum. The solid was dissolved in water (10 mL) and 70% w/w HClO$_4$ (250 µL) was added. The solution was concentrated and dried under high vacuum overnight. The solid was then washed with EtOAc and concentrated (3×10 mL). After decanting the supernatant, the pellet was dried under high vacuum affording 7 as a white powder (0.150 g, 0.264 mmol, 89%). M.p. >350° C. (dec). IR (KBr, cm$^-$): 3239s, 2963w, 2920w, 2885w, 1748s, 1472m, 1445m, 1429m, 1371w, 1301m, 1254m, 1188m, 1122m, 1107m, 1076m, 1021m, 1006m. $^1$H NMR (400 MHz, D$_2$O): 5.43 (d, J=10.0, 2H), 5.24(d, J=11.2, 4H), 4.85 (d, J=16.0, 2H), 4.56 (d, J=11.2, 4H). $^{13}$C NMR (100 MHz, D$_2$O): 168.5, 166.9, 156.7, 81.3, 74.9, 72.3, 48.4. MS (FAB, Magic Bullet/PEG):

m/z 569 (100, [M+H]⁺). HR-MS (FAB, Magic Bullet/PEG): m/z 569.0884 ([M+H]⁺, $C_{18}H_{17}N_8O_{14}$, calcd 569.0864). X-ray crystal structure. Crystals obtained from $H_2O$.

Compound 8: This compound was prepared according to the literature procedure.

To a solution of pyromellitic dianhydride (5.00 g, 22.9 mmol) in hot acetic acid (250 mL) was added hydrazine monohydrate (2.52 g, 50.4 mmol) in AcOH (50 mL) and heated at reflux for 1 h. The reaction mixture was cooled to RT and filtered to yield a yellow powder. This powder was dissolved in hot sodium hydroxide (1M) and then precipitated with acetic acid (1.5 mL). The solution was filtered to give 7 as a pale yellow powder (4.03 g, 16.4 mmol, 71%). M.p. >350° C. IR (KBr, cm⁻¹): 2893m, 1662s, 1565m, 1518w, 1503w, 1359m, 1297m, 1184m. ¹H NMR (400 MHz, DMSO-d₆): 11.85 (br.s, 4H), 8.64 (br.s, 2H). MS (FAB, glycerol/HCl): m/z 247 (100, [M+H]⁺). HR-MS (FAB, glycerol/HCl): m/z 247.0467 ([M+H]⁺, $C_{10}H_7N_4O_4$, calcd 247.0466).

Compound 9: To a flask containing 8 (0.036 g, 0.147 mmol) was added anh. MeSO₃H (1 mL) and the mixture was stirred at 80° C. until homogenous. Compound 3C (0.100 g, 0.147 mmol) was added in one portion and the flask was sealed and heated at 80° C. for 3 h. The reaction mixture was allowed to cool and then poured into water (10 mL). The solid was collected by centrifugation and the resulting pallet was resuspended in water (10 mL) and centrifuged again. The solid was washed with acetone and centrifuged (2×10 mL) and then dried under high vacuum overnight which afforded 9 as a pale yellow powder (0.102 g, 0.537 mmol, 78%). M.p. >350° C. (dec). TLC (CHCl₃/MeOH, 3:2) $R_f$ 0.16. IR (KBr, cm⁻¹): 2982w, 2928w, 2847w, 1751s, 1647s, 1464s, 1441s, 1394w, 1375w, 1285s, 1258s, 1231s, 1165m, 1115m, 1091m, 1056m, 1025m. ¹H NMR (400 MHz, DMSO-d₆): 8.69 (s, 4H), 6.84 (d, J=15.8, 8H), 5.92 (d, J=16.3, 4H), 5.13 (d, J=15.8, 8H), 4.75(d, J=16.3, 4H), 4.31-4.24 (m, 16H), 1.29-1.21 (m, 24H). ¹³C NMR (100 MHz, TFA/D₂O capillary): 164.0, 163.1, 156.4, 155.3, 131.9, 130.2, 78.9, 78.4, 66.3, 66.2, 52.4, 48.9, 12.3, 12.2. MS (FAB, Magic Bullet/CsI): m/z 1913 (100, [M+Cs]⁺). HR-MS (FAB, Magic Bullet/CsI): m/z 1914. 3508 ([M+Cs]⁺, $^{12}C_{71}$ $^{13}CH_{68}N_{24}O_{32}Cs$, calcd 1914.3519).

Compound 10: To a flask containing 8 (12.0 mg, 0.0470 mmol) was added anh. MeSO₃H (1 mL) and the mixture was stirred at 80° C. until homogeneous. Compound 5 (30.0 mg, 0.0470 mmol) was added in one portion and the flask was sealed and heated at 80° C. for 3 h. The reaction mixture was allowed to cool and then poured into water (10 mL). The solid was collected by centrifugation and the resulting pellet was resuspended in water (10 mL) and centrifuged again. The solid was washed with acetone and centrifuged (2×5 mL) and then dried under high vacuum overnight which afforded pure 10 as a pale yellow powder (28.0 mg, 0.0164 mmol, 70%). M.p. >350° C. (dec). TLC (CHCl₃/MeOH, 3:1) $R_f$ 0.18. IR (KBr, cm⁻¹): 2959w, 2932w, 2870w, 1759s, 1716s, 1643s, 1526s, 1456s, 1433s, 1386m, 1344m, 1309s, 1254s, 1173m, 1146m, 1111m, 1068m, 1048m, 1021m. ¹H NMR (400 MHz, CD₃CN): 8.87 (s, 4H), 7.04 (d, J=15.8, 8H), 5.55 (d, J=15.8, 4H), 5.28(d, J=15.8, 8H), 5.13 (d, J=15.8, 4H), 3.54(t, J=7.2, 8H), 1.62 (m, 8H), 1.35 (m, 8H), 0.94(t, J=7.2, 12H). ¹³C NMR (100 MHz, TFA/D₂O capillary): 167.2, 165.2, 156.0, 153.7, 131.5, 129.8, 71.1, 70.6, 51.5, 46.8, 40.1, 28.2, 19.1, 11.2. MS (FAB, Magic Bullet/CsI): m/z 1837(100, [M+Cs]⁺). HR-MS (FAB, Magic Bullet/CsI): m/z 1837.3623 ([M+Cs]⁺, $C_{72}H_{64}N_{28}O_{24}Cs$, calcd 1837.3703). X-ray crystal structure. Crystal obtained from CH₃CN.

Compound 11: To a flask containing 8 (17.0 mg, 0.0700 mmol) was added anh. MeSO₃H (1 mL) and the mixture was stirred at 80° C. until homogeneous. Compound 6 (40.0 mg, 0.0700 mmol) was added in one portion and the flask was sealed and heated at 80° C. for 3 h. The reaction mixture was cooled to RT and then poured into a water/acetone mixture (1:1, 10 mL). The solid was collected by centrifugation and the resulting pellet was resuspended in acetone, centrifuged (2×10 mL) and then dried under high vacuum overnight which afforded 11 as a pale yellow powder (35.0 mg, 0.0224 mmol, 65%). M.p. >350° C. (dec). IR (KBr, cm⁻¹): 3418s, 2963w, 2932w, 2917w, 1740s, 1697m, 1685m, 1647s, 1635s, 1460m, 1417w, 1383w, 1289m, 1262m, 1239m, 1161m, 1111m, 1049m. 1H NMR (400 MHz, DMSO-d₆): 8.67 (s, 4H), 6.83 (d, J=15.8, 8H), 5.75 (d, J=15.8, 4H) 5.04 (d, J=15.8, 8H), 5.02 (d, J=15.8, 4H). ¹³C NMR (100 MHz, DMSO-d₆): 166.5, 165.7, 154.9, 154.3, 132.0, 128.2, 78.8, 77.6, 51.2, 48.2. ES-MS: m/z 1557 (100, [M+H]⁺).

Compound 12: To flask containing 8 (0.672 g, 2.73 mmol) was added anh. MeSO₃H (10 mL) and the mixture was stirred at 80° C. until homogeneous. Compound 2 (1.00 g, 2.73 mmol) was added in one portion and the flask was sealed and heated at 80° C. for 3 h. The reaction mixture was allowed to cool and then poured into water (100 mL). The yellow precipitate was collected by filtration over a medium fritted funnel and washed with water (50 mL) until dry. The solid was suspended in acetone (150 mL), stirred for 30 min., and filtered. The filtrate was concentrated and dried under high vacuum to yield 0.250 g of crude material. Flash chromatography (5:1 CHCl₃/MeOH) gave 12 as a pale yellow solid (0.125 g, 0.085 mmol, 6.3%). M.p. >350° C. (dec). TLC (CHCl₃/MeOH, 4:1) $R_f$ 0.11. IR (KBr, cm⁻¹): 2982 w, 2963w, 2928w, 1755s, 1654s, 1441s, 1425s, 1386m, 1731m, 1305s, 1262s, 1235s, 1153m, 1091m, 1021m. ¹H NMR (400 MHz, CD₃CN): 8.80 (s, 4H), 7.06 (d, J=16.1, 4H), 7.05 (d, J=16.1, 4H), 5.95 (d, J=16.3, 2H), 4.92 (d, J=16.1, 4H), 4.86 (d, J=16.1, 4H), 4.78(d, J=16.3, 2H), 4.37(q, J=7.1, 4H), 4.34-4.27 (m, 8H), 1.36-1.26 (m, 18H), ¹³C NMR (100 MHz, DMSO-d₆): 164.7, 164.3, 164.0, 154.4, 153.7, 153.6, 132.1, 131.6, 128.4, 78.3, 77.2, 77.1, 65. 3, 65.0, 64.9, 50.1, 48.3, 14.0, 13.9 (only 20 of the 22 expected resonances were observed). MS (FAB, Magic Bullet/PEG): m/z 1471 (100, [M+H]⁺). HR-MS (FAB, Magic Bullet): m/z 1603.2550 ([M+Cs]⁺, $C_{60}H_{54}N_{20}O_{26}Cs$, calcd 1603.2572).

Compound (±)-13: To a flask containing 8 (36.0 mg, 0.147 mmol) was added anhydrous MeDO₃H (1 mL) and the mixture was stirred at 80° C. until homogeneous. Compound 4CC (0.146 g, 0.147 mmol) was added in one portion and the flask was sealed and heated at 80° C. for 3 h. The reaction mixture was cooled to RT and then poured into water (10 mL). The solid was collected by centrifugation and the resulting pellet was resuspended in water (10 mL) and centrifuged again. The solid was washed with water/acetone (1:1, 10 mL), centrifuged and dried under high vacuum overnight to yield 0.140 g of impure (±)-13 as a yellow solid. Flash chromatography (5:1:0.5 CHCl₃/MeOH CH₃CN) gave (±)-13 as a pale yellow solid (0.104 g, 0.0490 mmol, 67%). M.p. >350° C. (dec). TLC (CHCl₃/MeOH CH₃CN, 5:1:0.5) $R_f$ 0.23. IR (KBr, cm⁻¹):2977w, 2958w, 2920w, 2848w, 1757s, 1644m, 1451s, 1259s, 1232s, 1164w, 1085m, 1017s. ¹H NMR (400 MHz, DMSO-d₆): 8.77 (s, 2H), 8.61

(s, 2H), 6.91 (d, J=15.5, 2H), 6.80(d, J=16.0, 2H), 5.95(d, J=16.0, 4H), 5.86(d, J=16.3, 2H), 5.81(d, J=16.3, 2H), 5.17(d, J=15.5, 2H). 5.13 (d, J=16.0, 2H), 4.78 (d, J=16.3, 2H), 4.61(d, J=16.0, 2H), 4.59(s, 2H), 4.40(d, J=16.3, 2H), 4.29-4.14(m, 20H), 4.09(d, J=16.0, 2H), 3.97(q, J=7.0, 4H), 1.27-1.09 (m, 36H). $^{13}$C NMR (10 MHz, DMSO-$d_6$): 165.7, 165.6, 165.3, 165.2, 164.7, 156.2, 155.1, 154.8, 154.5, 154.2, 133.2, 132.5, 81.1, 79.6, 79.5, 78.8, 78.1, 77.1, 65.5, 64.6, 64.1, 51.2, 48.8, 14.4, 13.9 (only 25 of the 42 expected resonances were observed). ES-MS: m/z 1060.5 (100, [M+2H]$^{2+}$).

In accordance with the present invention, hydrazides function as nucleophilic glycoluril surrogates in typical methylene bridge forming reactions. We have also discovered that pyridazine 15 undergoes rapid reaction with 16 yielding 17 forming (Scheme 3). Products arising from the self-condensation of 16 were not detected, which indicates that 15 is a highly competent nucleophile in typical methylene bridge forming reactions. The high reactivity of 15 can be ascribed to the alpha-effect. Heating 17 and phthalhydrazide 18 in dichloroethane containing anhydrous PTSA (p-toluenesulforic acid) resulted in the clean formation of 19. We draw two conclusions from this experiment: 1) the formation of methylene bridges between pyridazine and glycoluril is a reversible process, and 2) phthalhydrazide 18 can replace pyridazine 15, presumably because 15 regains aromaticity in the process.

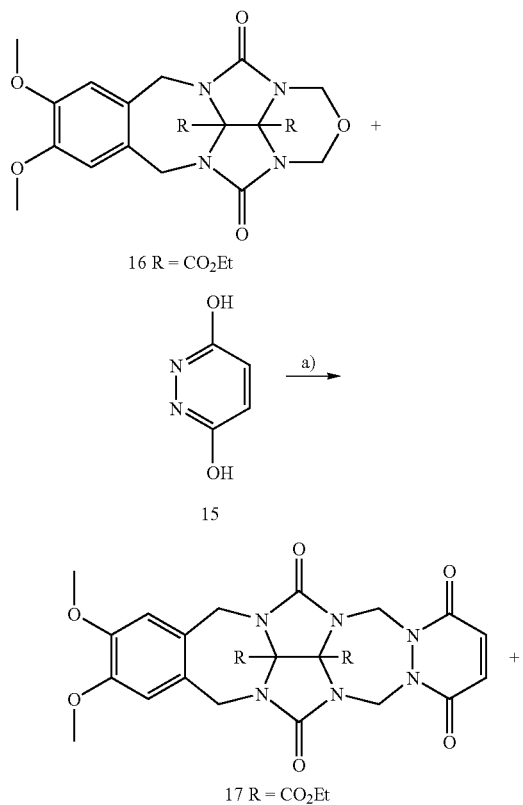

Scheme 3.
Surrogates for glycoluril in CB[n] formation
Conditions: a) TFA, reflux, 55%, b) PTSA, ClCH$_2$CH$_2$Cl, reflux, 71%.

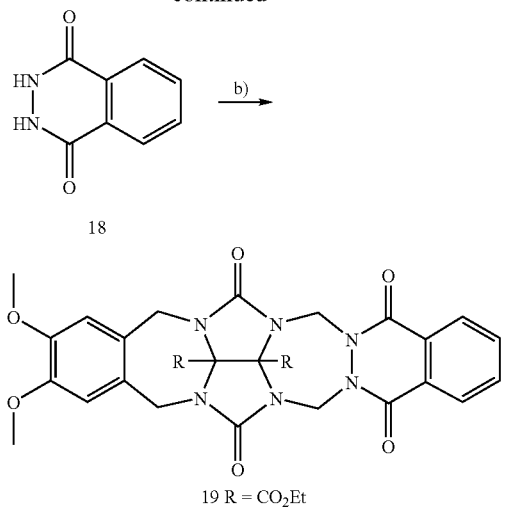

Second, the present invention may be used to prepare cyclic ether-terminated glycoluril oligomers.

Synthesis of cyclic ether terminated glycoluril oligomers. To date, all known CB[n] forming reactions have relied on the reaction of glycoluril and its derivatives and/or the corresponding bis (cyclic ether) derivatives. In such reactions, numerous CB[n] derivatives with different values of 'n' and different patterns of their substituents are theoretically possible and experimentally observed. To overcome these statistical constraints, we have provided methods for the selective preparation of CB[n] with specific values of n by a building block approach.

Third, the present invention affords for the incorporation of bis (phthalhydrazide) into CB[n] derivatives by macrocyclization. The results described above indicates that bis (phthalhydrazide) functions well as a glycoluril surrogate in CB[n] analog forming reactions.

Further, the present invention provides synthetic methods for preparing methylene-bridged glycoluril dimers as well as a mechanism of interconversion of their S- and C-shaped Diastereomers. We have also discovered as shown in Scheme 4 that the condensation of 1 eq. of latent electrophile cyclic ether 9 and 1 eq. of latent nucleophile (±)-10 under anhydrous acidic conditions (ClCH$_2$CH$_2$Cl, anh. PTSA, reflux) selectively yields the C-shaped heterodimer (±)-11 in high yield (Scheme 4a). This experiment establishes that scrambling does not occur under anhydrous acidic conditions, and that kinetic considerations can be used to control the substitution pattern. Two diastereomers are formed as kinetic products, the S-shaped and C-shaped dimers. In any synthesis of CB[n] derivatives, it is only the C-shaped forms that lead to product. Therefore, an understanding of the interconversion of the S- and C-shaped forms is crucial. We have established that the C-shaped form is thermodynamically more stable than the S-shaped form by 2 kcal mol$^{-1}$. The S- to C-shaped isomerization reaction allowed us to distinguish between three different isomerization mechanisms and establishes the isomerization as a diastereoselective and intramolecular process (Scheme 4b). In essence the two halves of (±)-12 rotate 180° with respect to one another without ever becoming disconnected yielding (±)-13. These two results indicate that under anhydrous acidic conditions suitable combinations of nucleophilic and electrophilic glycoluril derivatives afford control over the size and pattern of substituents during the synthesis of cucurbit[n]uril derivatives. For example, the reaction of $3_H$ with $4_{CO2Et}$ could deliver CB[6], CB[8], and CB[10] analogs 14[n] in which the substituents alternate (Scheme 4c). The compound numbers used in this paragraph refer only to the compounds shown in Scheme 4.

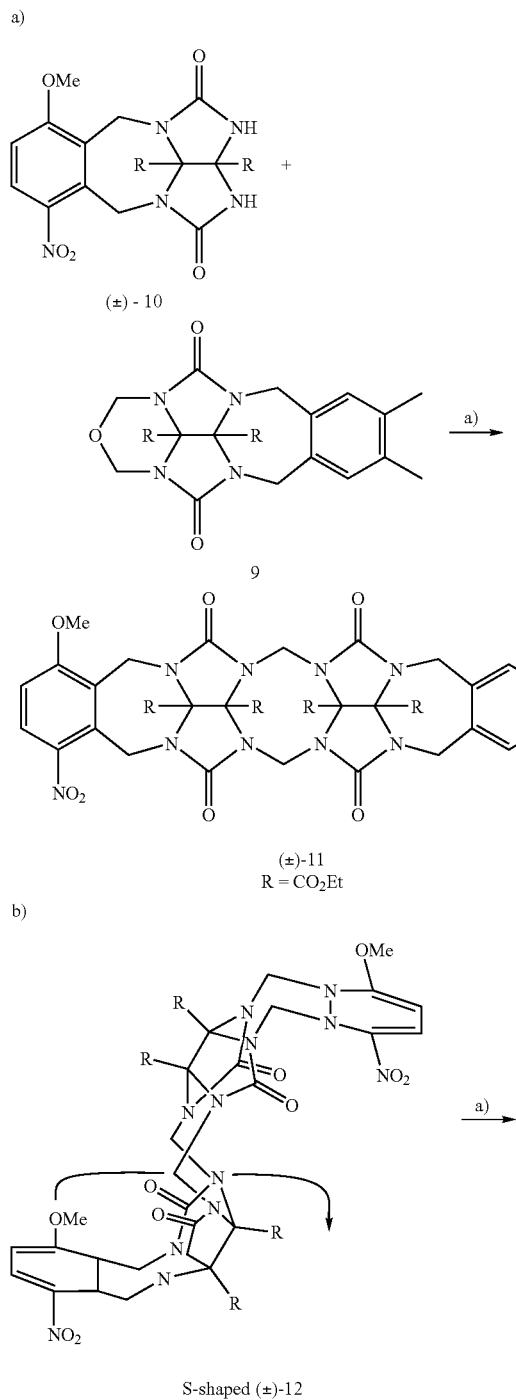
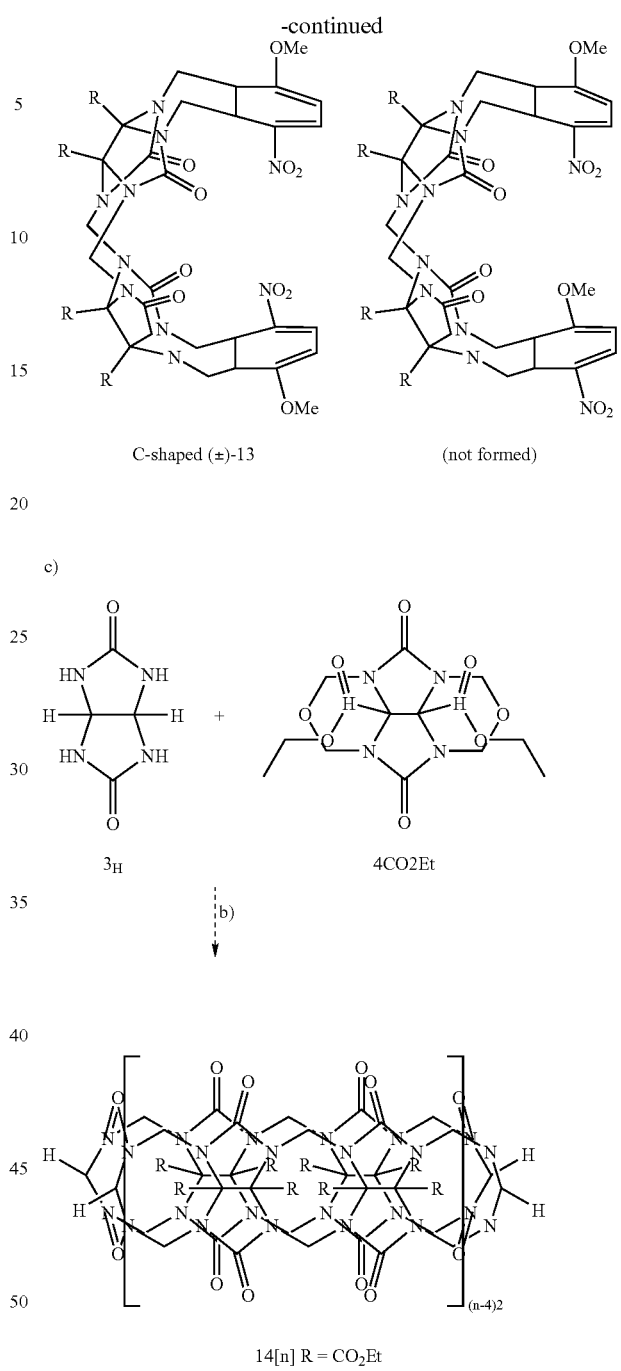

The extension of the building block approach to CB[7] and CB[8] analogs is now described (Schemes 5 and 6). Notably, the reaction between all C-shaped methylene bridged glycoluril trimer 22 and 28 affords the CB[8] analog 38 selectively. Similarly, a mixture of 20, 22, and 28 is expected to yield CB[6], CB[8] analogs 29, 38, and CB[7] analog 39 Scheme 6. Compounds 38 and 39 are more highly strained than their CB[5] and CB[6] counterparts, but form since their building blocks are predisposed to do little else. Advantageously, compounds 38 and 39 offer much more spacious cavities for molecular recognition processes. The cavity dimensions of 38 amounts to 10.0 Å wide by 18.4 Å long whereas 39 is 8.8 Å wide by 16.8 Å long.

Scheme 5.
Synthesis of glycoluril oligomers and x-ray crystal structure of 21.
Conditions: a) ClCH$_2$CH$_2$Cl, (CH$_2$O)$_n$, PTSA, reflux
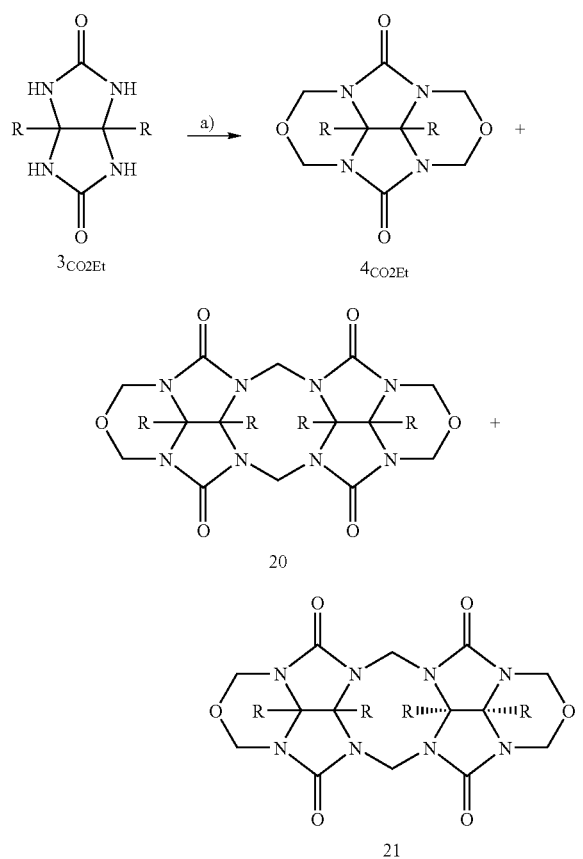
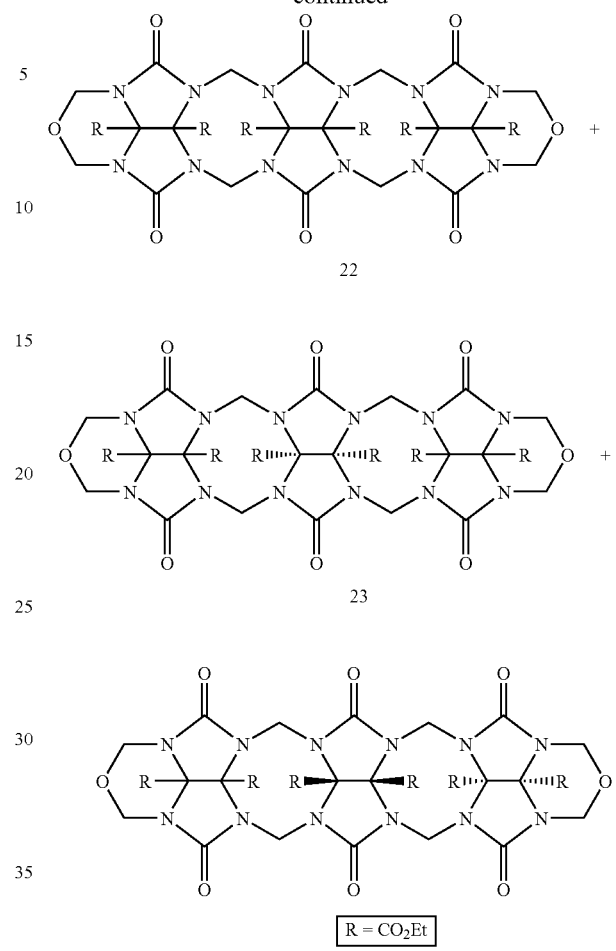
R = CO$_2$Et
Scheme 6.
Synthesis of CB[8] and CB[7] analogs.
Conditions: a) MeSO$_3$H, 80° C.
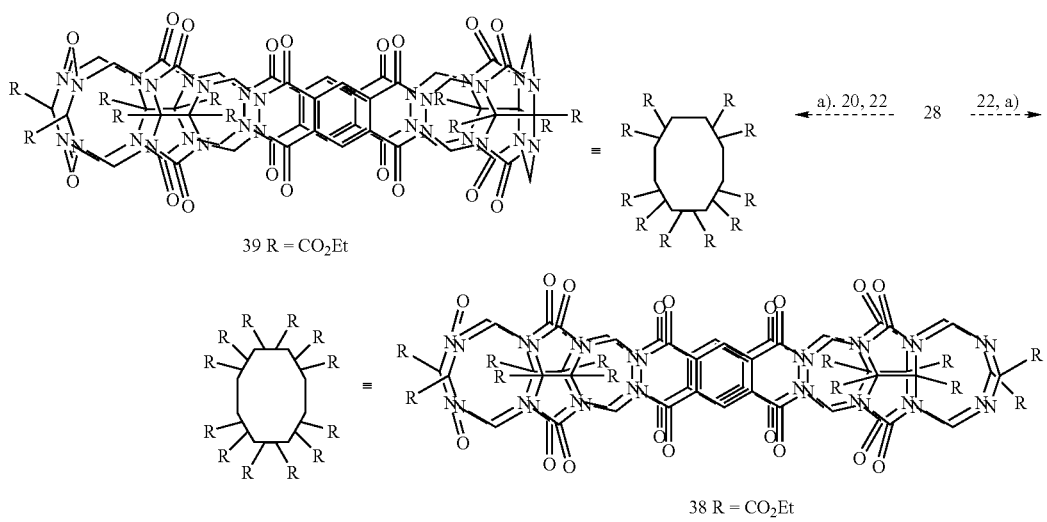

If the event that the synthesis of CB[8] analog 38 is unsuccessful due to polymerization, the alternative route described in Scheme 7 may be used. The tennis ball monomers with benzene (40) and naphthalene (41) spacers prepared by Rebek may be transformed into the corresponding bis(cyclic ethers) 42 and 43 by our efficient procedures. Compounds 42 and 43 are reacted with 28 in MeSO$_3$H to yield the CB[8] analogs 44 and 45. In the formation of 44 and 45, the benzene and naphthalene spacers eliminate the steric interactions that occur between neighboring glycoluril rings and also eliminate the possibility of reversible formation of the methylene bridged glycoluril dimer substructure. Compound 44 has estimated dimensions of 9.6 Å by 17.2 Å whereas 45 has dimensions of 12.0 Å by 16.8 Å.

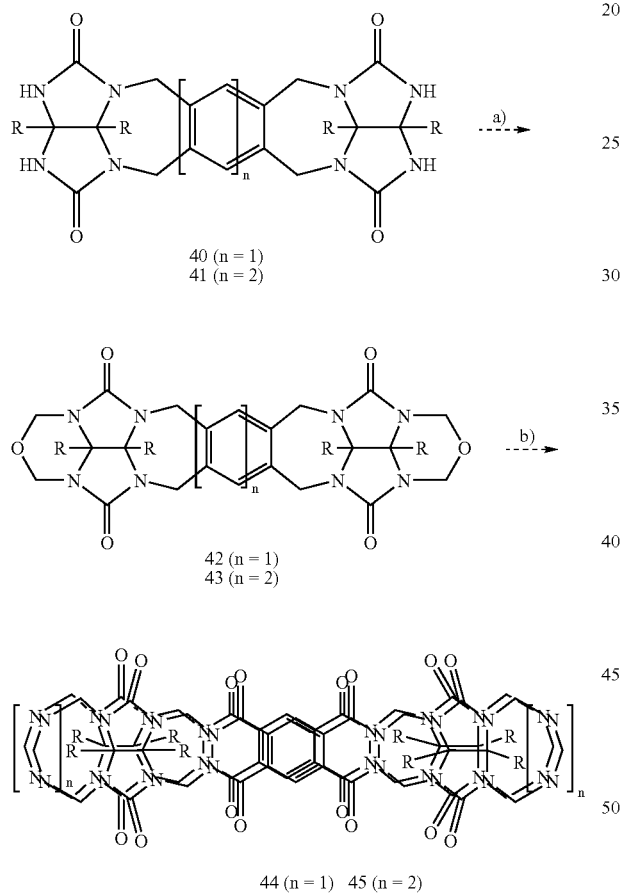

Scheme 7.
Synthesis of CB[8] analogs. Conditions: a) TFA, (CH$_2$O)$_n$, 70° C., b) 28, MeSO$_3$, 80° C.

40 (n = 1)
41 (n = 2)

42 (n = 1)
43 (n = 2)

44 (n = 1)  45 (n = 2)

The Formation of Termolecular Complexes

Nature is replete with examples of host-guest complexes involving multiple species.

However, relatively few systems enforce intimate contact between multiple guest species. One reason for this deficiency is the synthetic challenge posed by creating cavities large enough to simultaneously bind two or more molecules. Some large organic hosts connected by covalent bonds that are potentially capable of binding two or more guest includes Cram's carcerands, Sherman's bis- and tris-carcerands, and Kim's CB[8]. Among the systems held together by non-covalent bonds, Fujita's octahedron, Stang's dodecahedron, Rebek's dimeric capsules, and the hexameric resorcinarenes first described by Atwood are prominent examples. Of the cucurbiturils only CB [8] has been used to systematically study the formation of ter- and higher molecularity complexes.

However, the cavities of the present CB[n] compounds offer unique advantages for forming host-guest complexes. For example, the CB[6] analogs: 1) possess two well defined high-affinity binding sites (H-bonding to ureidyl C=O) that allows binding of quest molecules with predictable geometry, 2) orient their guests such that sizable amounts of surface area between the two (or more) guests will interact, 3) their length, width, height, and chemical functionality can be modified by modular synthesis, and 4) just like a few conventional complexes their binding processes are typically in the slow exchange regime on the chemical shift time scale which allows detailed structural investigations and the simultaneous observation of all populated complexes.

For example, many classes of guests, such as those shown below, form well-defined complexes with the new CB[n] analogs by a combination of H-bonds, π-π, and ion-dipole interactions.

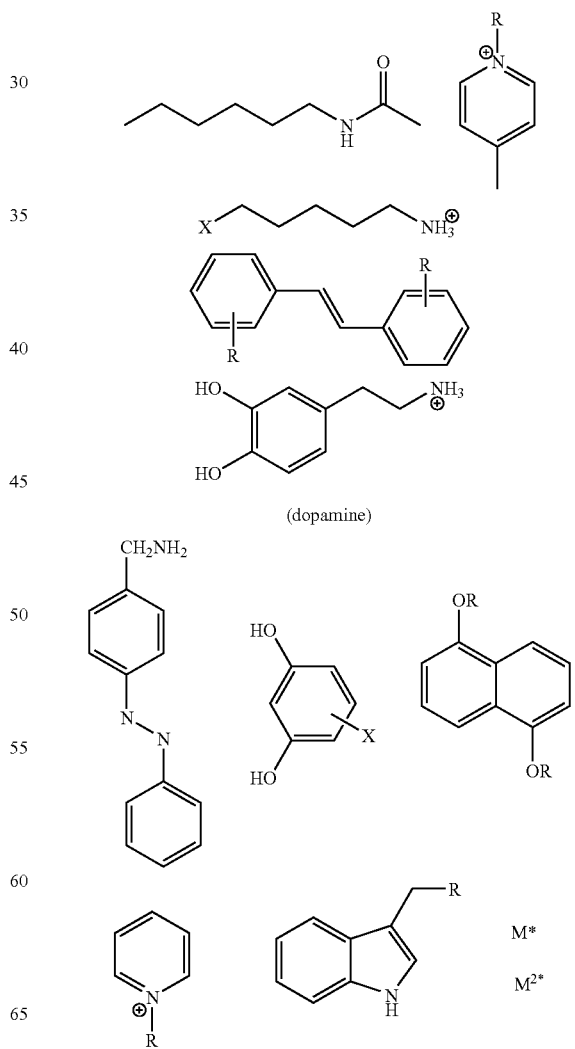

(dopamine)

-continued

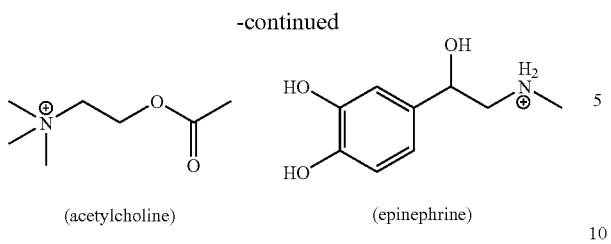

(acetylcholine)   (epinephrine)

Exemplary guests for CB[n] analogs of the present invention.

However, other types of compounds may be used as guests, such as dye stuffs, nucleic acids, aromatic compounds, amino acids, explosives, such as trinitrotoluene (TNT), peptides or even amino sugars.

The cavity defined by $D_{2h}$-symmetric CB[6] analog 29 measures 7.0 Å wide by 15.1 Å long and its roomy enough to accommodate at least two guest molecules (Scheme 8). Consider the stepwise binding of two molecules of hexylacetamide (one of the compounds shown above) and denoted as "64" in $CDCl_3$. As the first molecule of 64 binds, the $D_{2h}$-symmeric host is transformed into a $C_s$-symmetric host-guest complex. The distal end of the 29•64 complex this has a chemically distinct top and bottom. The binding of a second equivalent of 64 can, therefore, result in ether $C_{2v}$- or $C_{2h}$-symmetric diastereomeric complexes. The equilibrium between these two diastereomers is, of course, controlled by the precise non-covalent interactions between the two equivalents of 64. For most hosts, the equilibrium between these two diastereomers would be fast on the NMR time scale which would make it impossible to glean structural information about the structures of the two diastereomers. For 29, however, as with CB [6] itself kinetically stable complexes will be formed. When that occurs, values of ΔG for the equilibrium between the diastereomers can be derived and structural information may be obtained by $^1$H NMR. The four protons on the central aromatic ring of 29 report the symmetry of the termolecular complex since they are equivalent in $C_{2h}$-29•64•64 whereas there are two chemically non-equivalent sets in $C_{2v}$-29•64•64. The $C_{2h}$-symmetric form is preferred due to unfavorable electrostatic interactions between the amide carbonyl groups in the $C_{2v}$-symmetric form.

Scheme 8
Binding of 2 eq. of 64 into the cavity of 29 in $CDCl_3$ affords two diastereomers.

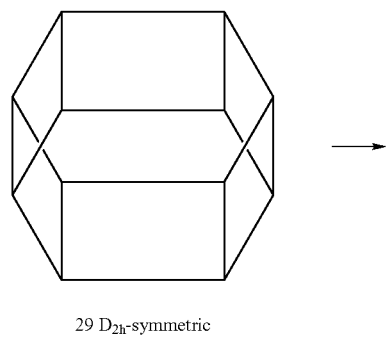

29 $D_{2h}$-symmetric

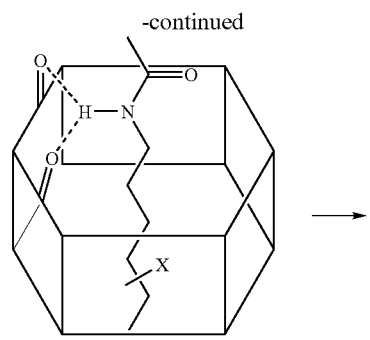

29-64 $C_s$-symmetric

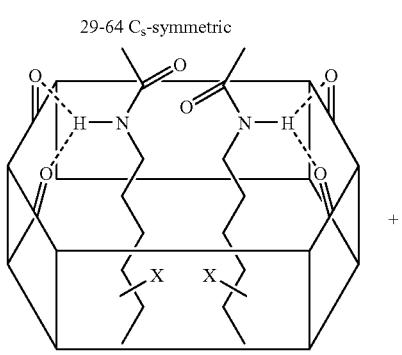

29-64-64 $C_{2v}$-symmetric

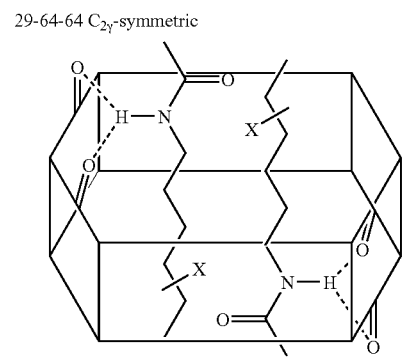

29-64-64 $C_{2h}$-symmetric

These are several strategies that may be used to control the equilibrium between the diastereomers (Scheme 8). For example, the complex between 29 and benzylacetamide (76) in $CDCl_3$ favors the $C_{2h}$-symmetric form due to unfavorable steric interactions between the two phenyl rings in the $C_{2v}$-symmetric form. An alternative approach relies on the identification of self-complementary guests that are capable of head-to tail interaction in the termolecular complex. For example, diamide 77 dimerizes in $CDCl_3$ solution to expose two amide NH groups which then bind to the carbonyl lined portals of 29. A similar approach relies on the covalent connection of two recognition elements that fold back upon itself to completely fill the cavity. Scheme 9c shows the complex between 52 and 78 which undergoes a folding process to maximize H-bond and π-π interactions. If the corresponding 2:2 complex competes with the formation of 52•78, the equilibrium toward 52•78 may be biased by changes to the linking diphenylglycine residue. The complex 52•78 serves as a gating element in membrane channels described further below.

Scheme 9.
Methods to control the head-to-head versus head-to-tail equilibrium:
a) steric, b) H-bonding, and c) folding.

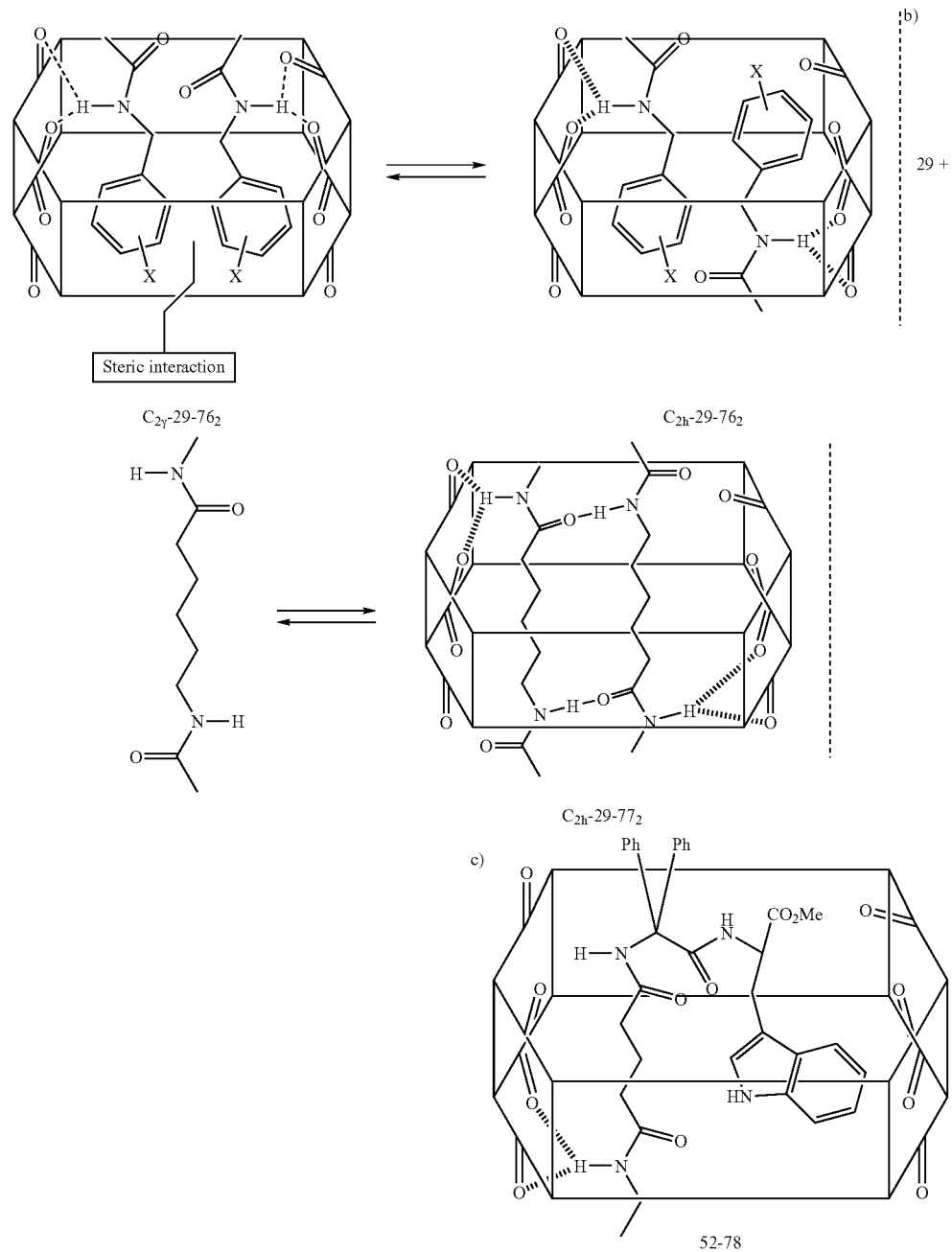

A problem that is intimately related to the ability of enzymes to catalyze reactions in their active sites, is the selective formation of heteromeric termolecular complexes. To control the nature of termolecular complexes it is important to both favor the desired heteromeric complex and simultaneously to disfavor the corresponding homomeric complexes. Our strategy to achieve such a result relies on the use of unfavorable steric interactions to disfavor certain complexes. This strategy is related to the "bumps and holes" approach that has been successfully used to modify protein binding sites. Consider, for example, the interaction of 29 with 79 (Scheme 10). The formation of this complex results in the filling of over 50% of the space available to guest molecules. The inclusion of a second molecule of 79, therefore, is disfavored on steric grounds and the remaining volume is available for a second, slimmer guest 80. The implicit assumption behind such an argument is that the homomeric termolecular complex 29•80$_2$ is thermodynamically less stable than the heteromeric complex. Aside from entropic advantages to forming the heteromeric termolecular complex, there are potential on enthaplic energetic gains. For example, the heteromeric termolecular complex benefits from additional favorable van der Waals interactions between the two guests whereas the two slimmer guests of the homomeric termolecular complex do not form a well packed interfacial region. Another but less elegant, approach to this problem relies on the relative thermodynamics of binding of 79 and 80. If 80 binds less tightly to 29 than 79 does—by using a mono-amide rather than a diamide—then the formation of the homomeric termolecular complex will be disfavored resulting in heteromeric termolecular complex formation.

the acetylcholine receptor, the potassium channel, gramicidin, amphotericin, and gap junctions. The beauty and wide range of functions of these natural systems has served as inspiration for biologists and bioorganic chemists alike. Amongst biologist and biochemists these investigations have most commonly involved the study of known channel forming proteins and peptides. A preeminent example is the x-ray crystal structure of the Kcs-K$^+$ selective channel, which confirmed many of the details inferred from biophysical studies. Bioorganic chemists, on the other hand, typically construct minimalist model systems or modify natural systems to address specific issues in channel function. Despite

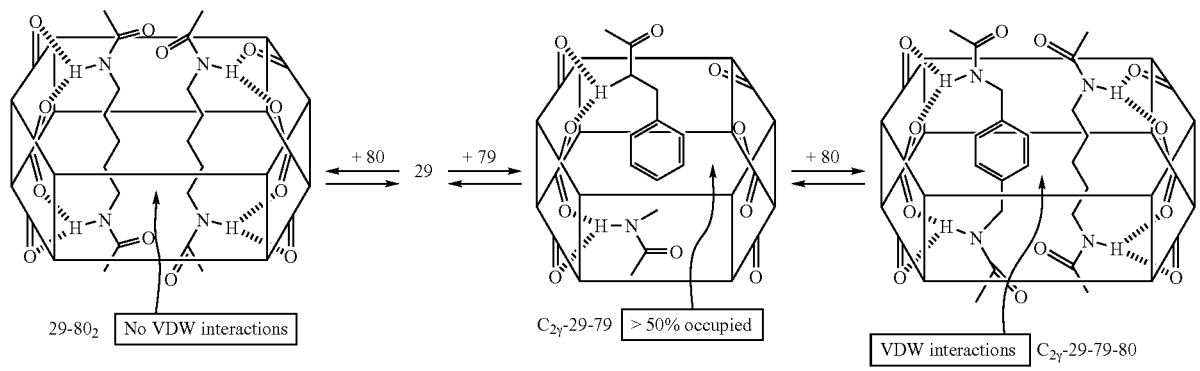

Scheme 10.
Selective preparation of heteromeric Termolecular complexes.

Cucurbit [6] uril Analogs as Active Components in Membranes. The plasma membrane, consisting mainly of lipids and proteins, separates individual cells from their environment. The functions performed by these membrane proteins allow cells to communicate with their environment and are crucial for life. For example, cell membranes contain channels and pumps which monitor and control the ionic and molecular composition of the cell. Natural examples include the array of synthetic membrane transports that have been reported, there are relatively few designed synthetic systems that can be switched on (open) and off (closed) by suitable gating mechanisms (voltage, ligand, light, redox, and thermal). Advantageously, we disclose herein rotaxane derivatives of the present CB[n] analogs as ligand-gated channels capable of repeated on-off switching behavior.

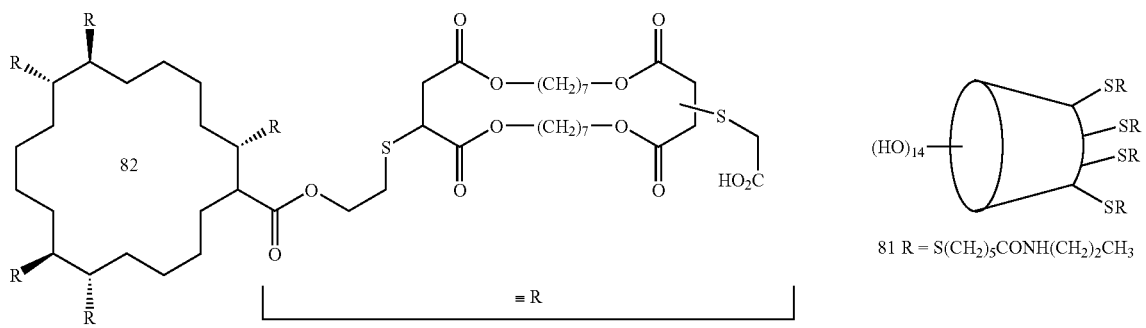

Scheme 11.
Examples of synthetic ion-channels.

81 R = S(CH$_2$)$_5$CONH(CH$_2$)$_2$CH$_3$

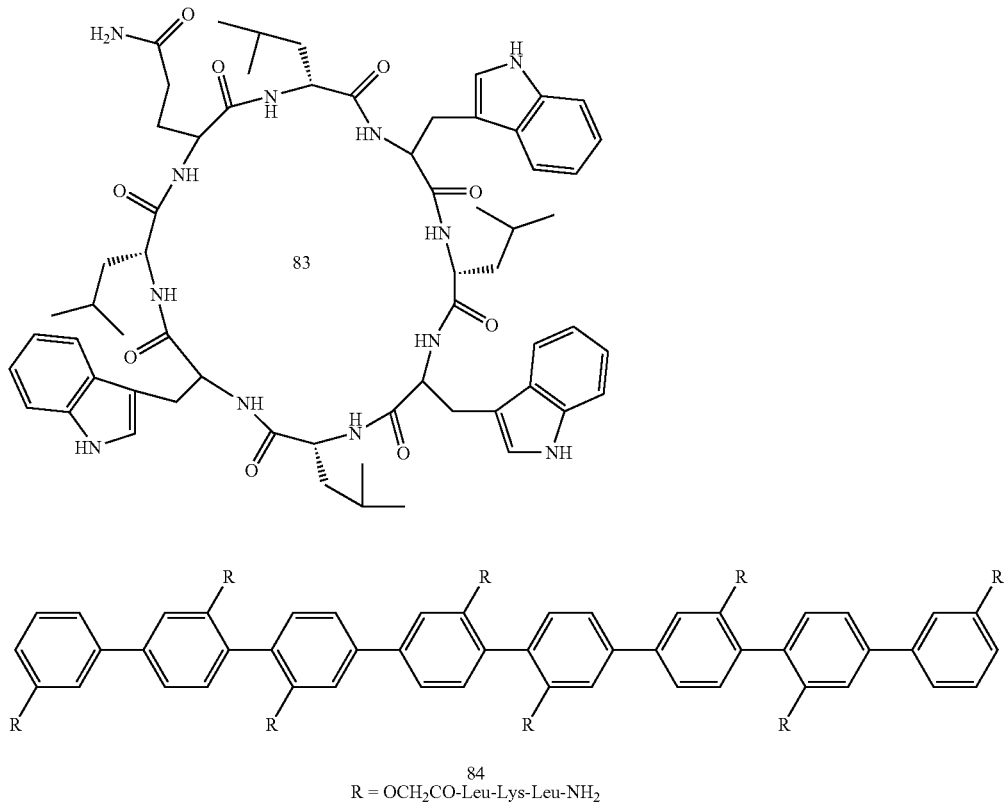

84
R = OCH₂CO-Leu-Lys-Leu-NH₂

Figure 4:
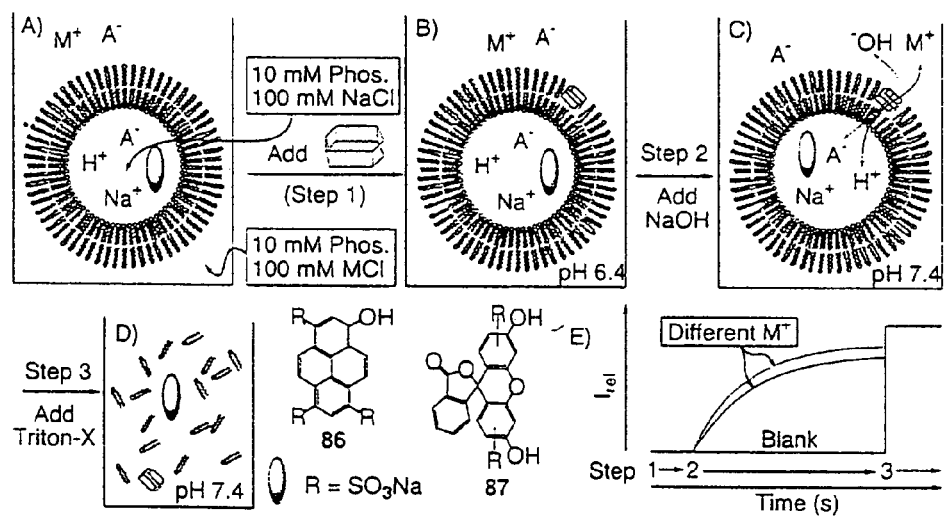
FIG. 4 illustrates electrolyte transfer experiments: A) LUVs containing intravesicular NaCl extravesicular MCl; B) after addition of 33, 35, 38 or 39; C) after addition of NaOH to adjust extravesicular pH to 7.4; D) after addition of Tritan-X 100; and E) fluorescence intensity versus time.

Monomeric CB[n] analogs as ion-carriers. Before we can contemplate the use of CB[n] analogs as components of more complicated transmembrane devices, it is necessary to determine the alkyl substituents needed to unsure that CB[n] analogs partition into lipid membranes and whether they act as artificial ion or molecular carriers. FIG. 4 shows a schematic representation of large unilamellar vesicles (LUVs) (85) that will be prepared from egg yolk L-α-phosphatidyl choline (EYPC) by hydration in pH 6.4, 10 mM phosphate containing 100 mM NaCl and 10 μM pyranine. Pyranine (86) is well known to act as a fluorescent pH indicator for vesicle interiors. The vesicular suspension may be subjected to many cycles of extrusion through a 0.1 μm polycarbonate membrane to afford LUVs with a diameter of 100 nm since vesicle diameter is known to influence their observed transport properties. Extravesicular dye is removed by size exclusion chromatography on Sephedex G-10. This stock solution of LUVs is diluted with pH 6.4, 10 mM phosphate buffer containing 100 mM metal halide salts (MX; M=Li⁺, Na⁺, K⁺, Cs⁺, X=Cl⁻, SO₄²⁻). These LUV's are treated with solutions of 33, 35, 38, and 39 in THF to introduce the CB[n] analogs into the membrane. To assay for their ability to transport ions across membranes, 1 pH unit gradient is induced across the membrane by the addition of NaOH to the extravesicular solution. This pH gradient induces the transport of H⁺ to the exterior or OH⁻ to the interior of the vesicles. The charges must be compensated by cation transport into the vesicle or anion transport out of the vesicle. With the known propensity of CB[6] to interact with cations, cation influx is facilitated. The change in intravesicular pH, which correlates linearly with the electrolyte exchange rate is measured by the ratiometric monitoring of the emission at 510 nm of 86 and 86⁻ (excitation at 403 and 460 nm). The initial pseudo-first order rate constants serve as a measure of the transport efficiency of 33, 35, 38, and 39. At the end of the experiments, the vesicles are lysed by the addition of the detergent Triton X-100 to establish the ratiometric fluorescence intensity at 100% electrolyte exchange. These pH induced transport experiments are performed with the full range of metal halide salts (LiCl, NaCl, KCl, and CsCl) with 33, 35, 38, and 39 to ascertain the cation selectivity for each of the CB[n] analogs. To confirm that any differences in transport rate for the different cations are, in fact, due to cation selectivity similar experiments may be performed using the corresponding sulfate salts. If the corresponding sulfate salts display similar transport rate and trends, it may then be concluded that the CB[n] analogs are cation selective. To exclude the possibility of defect formation induced by CB[n] analogs, vesicles filled with calcein (87, R=CH₂N(CH₂CO₂H)₂) are used. Calcein is a self-quenching dye whose fluorescence intensity is reduced by 95% at concentrations above 100 mM. Consider a solution of vesicles loaded with 120 mM 87. If the addition of 33, 35, 38, or 39 results on defects in the bilayer, 87 would be released from the vesicle, its concentration to drop below 100 mM due to dilution, and the fluorescence intensity would increase. If, however, the CB[n] analogs do not result in defects in bilayer, 87 would not be expected to be released and no increase in fluorescence intensity would be observed. The CB[n] compounds described above are shown in Scheme 12, 14, and 14 below.

Scheme 12.
Synthesis of CB[6] analogs. Conditions: a) BuNH$_2$, 70° C., 92%, b) PTSA, ClCH$_2$CH$_2$Cl, reflux, 46%, c) H$_2$O, MeOH, LiOH, d) MeSO$_3$H, 80° C.
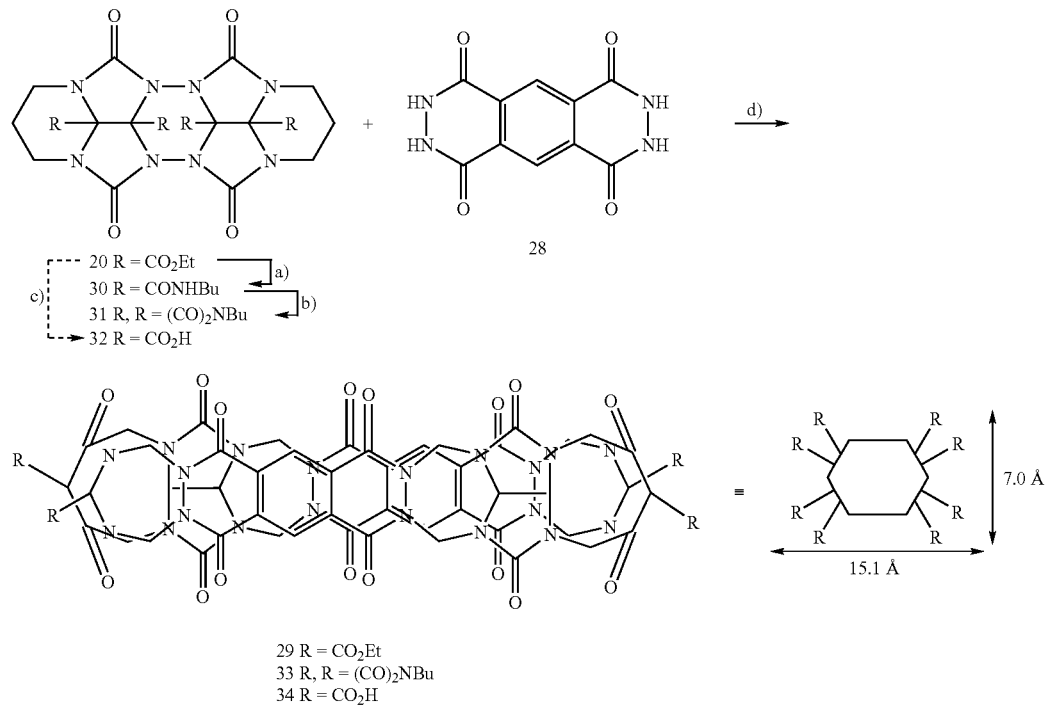
20 R = CO$_2$Et
30 R = CONHBu
31 R, R = (CO)$_2$NBu
32 R = CO$_2$H
28
29 R = CO$_2$Et
33 R, R = (CO)$_2$NBu
34 R = CO$_2$H
Scheme 13.
Synthesis of CB[5] analogs.
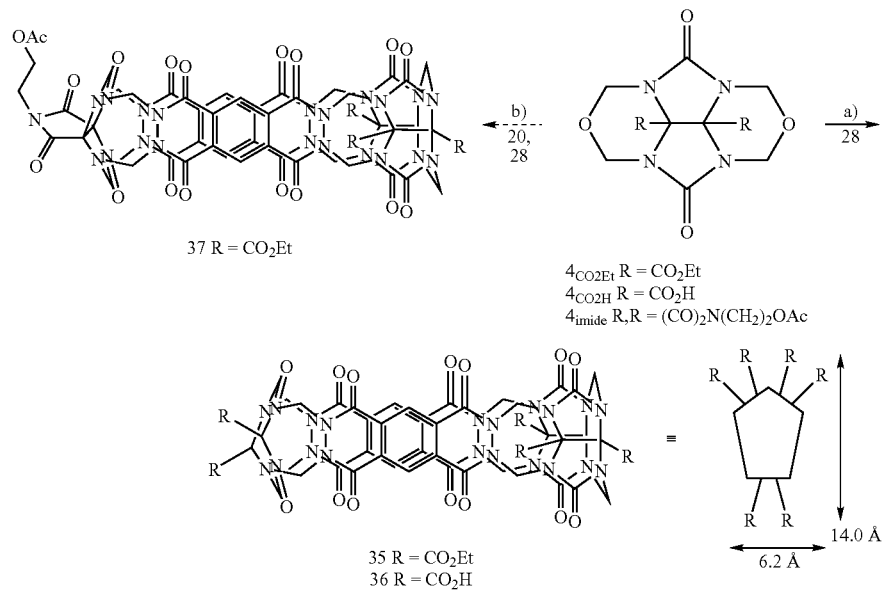
37 R = CO$_2$Et
4$_{CO2Et}$ R = CO$_2$Et
4$_{CO2H}$ R = CO$_2$H
4$_{imide}$ R, R = (CO)$_2$N(CH$_2$)$_2$OAc
35 R = CO$_2$Et
36 R = CO$_2$H Scheme 14.
Synthesis of CB[8] and CB[7] analogs.
Conditions: a) MeSO₃H, 80° C.

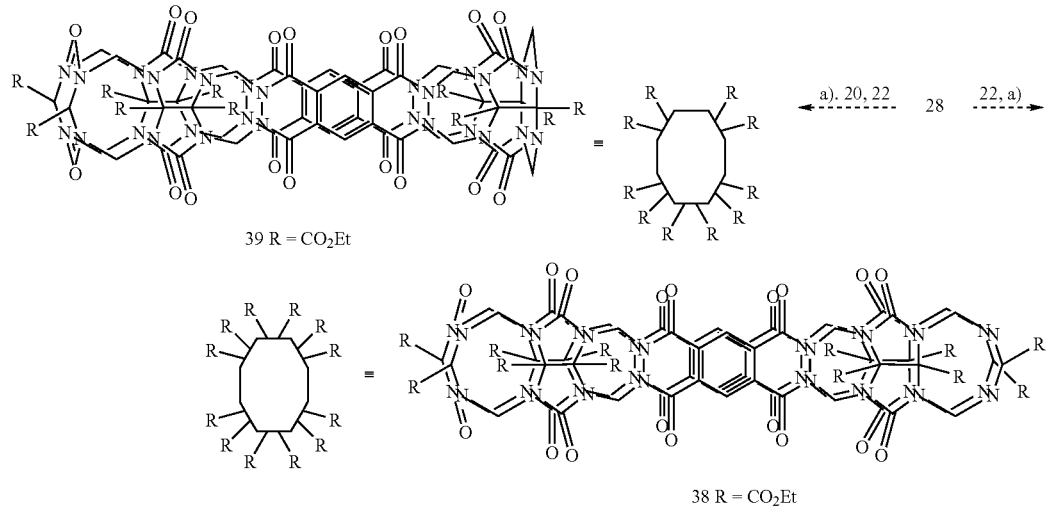

39 R = CO₂Et

38 R = CO₂Et

Figure 5:
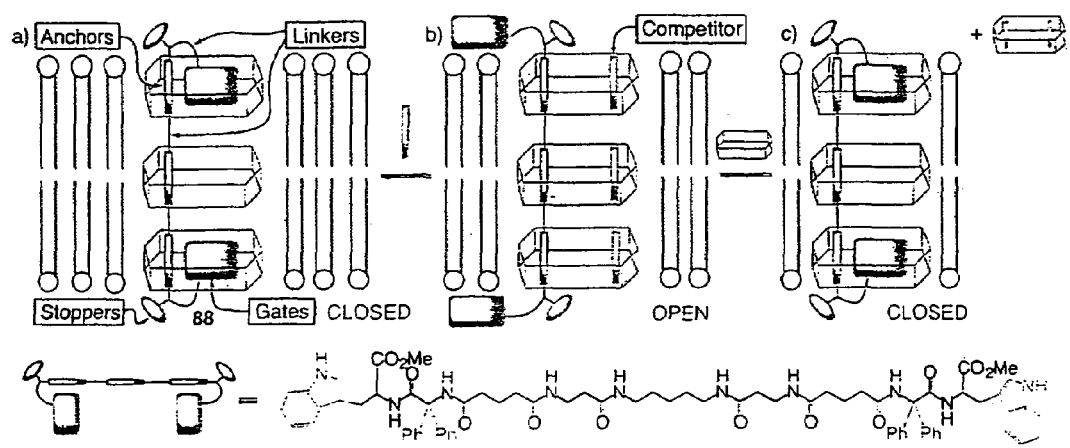
FIG. 5 illustrates a [CB] n-based ligand-gated ion-channel: a) functions of the various portions of 88 in the closed state; b) the open state; c) the addition of water-soluble CB[n] analog 53 sequesters the competitor and closes the gate.

Non-covalent synthesis of a Ligand-Gated Channel. The Stoddart group has pioneered the use of rotaxanes as functional components in molecular machines; these studies most frequently exploit the ability of rotaxanes to undergo controlled shuttling processes in response to physical or chemical stimuli. FIG. 5 shows a cartoon representation of a CB[6] tri-rotaxane 88 inserted into an EYPC bilayer that is capable of functioning as a ligand-gated channel. The function of tri-rotaxane 88 is not based on a shuttling process, rather it relies on a back-folding process. A tri-rotaxane is preferable since the width of the EYPC bilayer is 36 Å and the height of the CB[n] analogs is 9 Å, which when combined with the short linking elements (in black) spans the bilayer. Compound 88 was designed to contain three critical components (anchors, stoppers, and gates). Diamides as anchoring groups to promote the formation of the rotaxane since amides and resorcinols are known to bind tightly to acyclic glycoluril derivatives by the formation of hydrogen bonds in non-polar media similar to the interior of the membrane. To prevent decomplexation of the rotaxanes, we incorporated a diphenylglycine unit as a bulky stoppering group. Lastly, we selected an indole ring in the form of L-tryptophan as the gating element. We expect that the tryptophan ring will bind weakly into the cavity of 54 by π-π interactions. These elements will be connected by short linking units to form a symmetrical membrane spanning ensemble. In the absence of the ligand (FIG. 5a), the tryptophan residue will fold back into the cavity of the terminal rings (54). Examination of CPK models suggests that the tryptophan residue completely fills the available space in the cavity which closes the gate and impedes the transport of ions across the membrane. The addition of a soluble competitor that has higher affinity for the cavity of 54 results in the displacement of the gating groups and binding of 5 into the cavities of 54. If the competitor is narrower than the displaced tryptophan then the channel will be open. When 5 is used as competitor, CPK models suggest the diameter of the channel is 4 Å. The closing of the channel can then be achieved by the addition of water soluble CB[6] analog 53 which will sequester 5 allowing the gate to close.

Figure 6:
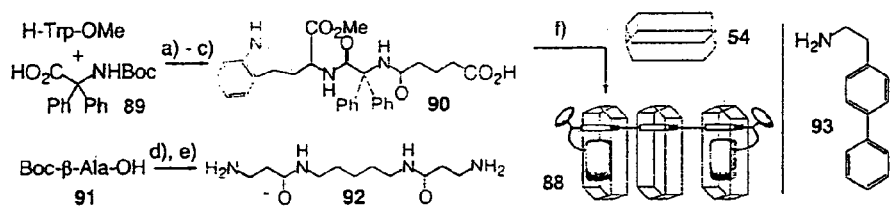
FIG. 6 illustrate a proposed synthesis of a tri-rotaxane.

Design and Synthesis of Rotaxanes. The preparation of rotaxanes based on CB[n] is well documented in the literature as a result of the pioneering work of Kim, Mock, and others. In the design and synthesis of tri-rotaxane 88, we take advantage of this literature precedent while paying close attention to making the symmetrical structure prepared by straightforward peptide bond forming reactions. The coupling of L-tryptophan methyl easter with 89 results in a gate-conjugate. Deprotection and elongation with glutaric anhydride yields the gate-stopper-anchor conjugate 90. Coupling of Boc protected β-alanine (91) with pentane diamine followed by deprotein yields 92 as the central anchoring group. The key rotaxane forming step is performed by peptide coupling 90 and 92 in non-polar CH₂Cl₂ solution in the presence of 54. In non-polar solvents where H-bonds are strong, 90 and 92 thread themselves into cavity of 54 by the formation of N—H•••O=C H-bonds. Reaction between nucleophile 54•92 and two equivalents of the activated ester of 54•90 yields the tri-rotaxane 88. Purification of 88 from side products containing fewer rings is accomplished by GPC since the CB[n] analogs have a molecular weight of around 2000. Although FIG. 6 describes the synthesis of tri-rotaxane 88 comprising CB[6] analog 54 and a tryptophan gate, this synthesis may be readily modified to prepare tri-rotaxanes incorporating the longer CB[6] analog 57 and an appropriate gating group like 2-(4biphenyl)ethylamine (93). Examination of CPK models suggests that the diameter of the channel formed upon gating with 5 is 6.5 Å which is suitable for the transport of small molecules. Analogous tri-rotaxanes incorporating CB[7] and CB[8] analogs 38 and 39 result in even more roomy channels.

Figure 7:
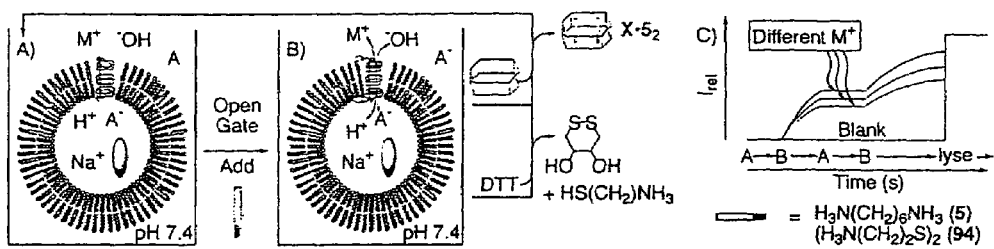
FIG. 7 illustrates a ligand-gated ion channel: a) closed, b) open and c) the fluorescence versus time profile.

The Gating Ligand Controls the Selectivity of the Channel. Compound 88 may be used as a ligand-gated ion channel. The fluorescence assay described above may be used to study the ion-carrier properties of the various CB[n] analogs. FIG. 7a shows vesicle incorporating 88 (closed) in their bilayer experiencing a 1 pH unit gradient. Upon addition of suitable ligands (5 or 94) the gates open (FIG. 7b) allowing cations to cross the membrane. The rate of ion transport is monitored by the fluorescence assay described above (FIG. 7c) for different extravesicular cations. The addition of water soluble CB[n] analog 53 closes the channel gated by 5 by competing for the gating ligand. Chemical reduction (DTT) serves to close channels gated by cysteamine (94). For this gating mechanism to be effective, it is necessary for the gating tryptophan to have higher affinity than 95 but lower affinity than 94. FIG. 6c shows the anticipated fluorescence versus time profile for two opening and closing cycles, however the fidelity of these channels is preferably tested over larger numbers of cycles. One of the unique aspects of tri-rotaxane 88 in its open state is that the gating ligand is an integral part of the channel that it has helped to form. The unique consequence is that the selectivity of channels formed from 88 are dependent on the chemical structure of the gating ligand. Thus, a single channel can selectively transport species in response to different gating ligands.

Although the above descriptions describe ligand-gated channels using the CB[6] analogs, the larger, CB[7] and CB[8] for example, analogs may also be used to transport molecules across the bilayer in ligand dependent fashion. Further, although ligand-gated processes have been described, the oligo-rotaxane design is well-suited for elaboration to light- and voltage-gated channels. For example, a light gated channel is realized using a truncated version of 88 lacking gates by employing azobenzene ligand 75. Voltage-gated processes are realized with cationic anchoring groups that undergo a shuttling process in response to applied potentials.

Finally, as noted above, the present cucurbit[n]uril compounds are guest compounds having cavities for host compounds. Generally, the cavity size of the CB[n] analogs is controlled by the length of the bis(phthalhydrazide) or functionally equivalent compounds used in one dimension. More specifically, the length of the glycoluril cycle ether will control the "height" of the cavity, which is usually about 9 Å, whereas the "length" of the cavity is controlled by the length of the bis(phthalhydrazide) or functional equivalent thereof.

Generally, the cavity of the CB[n] compound or analog will be sufficiently large to host a guest compound of up to a molecular weight of about 500. However, larger guests can be accommodated by the construction of larger cavities.

As noted above, the size of the cavity produced may be modified by the selection of glycoluril and bis(phthalhydrazide) in order to control size along two dimensions, length and height, in order to ultimately control cavity volume.

Further, as also noted aside from bis(phthalhydrazides) compounds which are functionally equivalent thereof may also be used. By "functionally equivalent" is meant serving the same function as bis(phthalhydrazides) in preparing cucurbit[n]uril compounds and analogs in accordance with the present invention. Generally, the functionally equivalent compounds contain units of the formula:

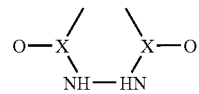

where the moiety (0-x) may be a carbonyl, sulfoxide or sulfone group. Further, the units may be part of the same ring system or where two separate such units are on separate ring system which rings are either fused or banded together via one or more spacer rings. The spacer rings may be saturated, unsaturated or aromatic, and are preferably 5- or 6-membered.

Finally, the term "guest" as used herein is defined as any compound or compounds which can reside within a cavity of the present cucurbit[n]uril compounds. Generally, the guest will have a molecular weight of up to about 750, and preferably up to about 500 (daltons). Examples of such guests are bioactive amines, such as epinephrine, dopamine, or alkaloids, such as morphine and other analgesics.

Generally, although cavity size, i.e. volume, will vary as noted above with the selection of glycoluril and bis(phthalhydrazide) or functional equivalent thereof, the preferred cavity size, i.e. volume, is up to about 8,000 Å$^3$, with corresponding dimensions of up to about 10 Å×20 Å×40 Å.

Having described the present invention, it will be readily apparent that many changes and modification may be made to the above-described embodiments without departing from the spirit and the scope of the present invention.

What is claimed is:

1. A cucurbituril compound comprising phthalhydrazide units in a macrocycle wall thereof, which compound is selected from the group consisting of CB[5], CB[6], CB[7] and CB[8] compounds.

2. The cucurbituril compound of claim 1, which is soluble in water or a polar organic solvent.

3. The cucurbituril compound of claim 2, wherein the polar organic solvent is selected from the group consisting of CHCl$_3$/MeOH, CH$_3$CN, DMSO, acetone, CH$_2$Cl$_2$ and DMF.

4. The cucurbituril compound of claim 1, having a broad absorption in CH$_3$CN of $\lambda_{max}$=342 nm.

5. The cucurbituril compound of claim 1, comprising at least two binding sites in an internal cavity thereof for complex formation.

6. The cucurbituril compound of claim 1, which is purifiable by silica gel column chromatography.

7. The cucurbituril compound of claim 1, which is a CB[5] compound having phthalhydrazide units in a macrocycle wall thereof.

8. The cucurbituril compound of claim 1, which is a CB[6] compound having phthalhydrazide units in a macrocycle wall thereof.

9. The cucurbituril compound of claim 1, which is a CB[7] compound having phthalhydrazide units in a macrocycle wall thereof.

10. The cucurbituril compound of claim 1, which is a CB[8] compound having phthalhydrazide units in a macrocycle wall thereof.

* * * * *